(12) United States Patent
Ghaboussi et al.

(10) Patent No.: US 8,070,679 B2
(45) Date of Patent: Dec. 6, 2011

(54) ACCURATE DETERMINATION OF INTRAOCULAR PRESSURE AND CHARACTERIZATION OF MECHANICAL PROPERTIES OF THE CORNEA

(75) Inventors: Jamshid Ghaboussi, Urbana, IL (US); David A. Pecknold, Champaign, IL (US); Youssef Hashash, Urbana, IL (US); Tae-Hyun Kwon, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 481 days.

(21) Appl. No.: 12/176,848

(22) Filed: Jul. 21, 2008

(65) Prior Publication Data

US 2009/0030300 A1 Jan. 29, 2009

Related U.S. Application Data

(60) Provisional application No. 60/951,260, filed on Jul. 23, 2007.

(51) Int. Cl.
*A61B 3/16* (2006.01)
(52) U.S. Cl. ..................................................... 600/399
(58) Field of Classification Search ........... 600/398–406
See application file for complete search history.

(56) References Cited

U.S. PATENT DOCUMENTS

| | | | | |
|---|---|---|---|---|
| 3,192,765 | A * | 7/1965 | Keiper | 600/398 |
| 2003/0069489 | A1* | 4/2003 | Abreu | 600/405 |
| 2003/0187343 | A1* | 10/2003 | Cuzzani et al. | 600/399 |
| 2003/0216894 | A1 | 11/2003 | Ghaboussi et al. | |
| 2004/0236204 | A1* | 11/2004 | Feldon et al. | 600/406 |
| 2005/0030473 | A1* | 2/2005 | Fahrenkrug et al. | 351/200 |
| 2006/0241437 | A1* | 10/2006 | Phillips et al. | 600/438 |
| 2007/0173713 | A1* | 7/2007 | Falck et al. | 600/405 |
| 2008/0086048 | A1* | 4/2008 | Dupps et al. | 600/405 |

OTHER PUBLICATIONS

Anderson, Kevin, et al., "Application of structural analysis to the mechanical behavior of the cornea," *J. R. Soc. Lond. Interface* 1:1-13 (2004).
Bryant, Michael R., et al., "Constitutive Laws for Biomechanical Modeling of Refractive Surgery," *Journal of Biomechanical Engineering* 118:473-481 (Nov. 1996).
Ehlers, Niels, et al., "Applanation Tonometry and Central Corneal Thickness," *ACTA Ophthalmological* 53:34-42 (1975).
Fung, Y.C., et al., "Pseudoelasticity of arteries and the choice of its mathematical expression," *Am J Physiol Heart Circ Physiol* 237(5):H620-H631 (Nov. 1979).
Fyfe, C.J., et al., "Numerical Modelling of the Indentation of Thin Corneas," retrieved from www.asbweb.org/conferences/2001/pdf/164.pdf, 2 pages (2001).
Hollman, Kyle W., et al., "Strain Imaging of Corneal Tissue With an Ultrasound Elasticity Microscope," *Cornea* 21(1):68-73 (2002).

(Continued)

*Primary Examiner* — Max Hindenburg
*Assistant Examiner* — Michael C Stout
(74) *Attorney, Agent, or Firm* — Nathan O. Greene; Brinks Hofer Gilson & Lione

(57) ABSTRACT

A computer-implemented method for accurate determination of intraocular pressure (IOP) and characterization of mechanical properties of a cornea is provided that includes measuring a cornea with a probe tonometer to produce at least force versus displacement data over a range of applied forces; and forming a model of corneal constitutive parameters, with a computer having a processor, based on the data obtained by the probe tonometer to more accurately determine IOP and characterize mechanical properties of the cornea, wherein the computer is coupled with the probe tonometer.

11 Claims, 14 Drawing Sheets

OTHER PUBLICATIONS

Huang, T, et al., "Corneal Curvature Change Due to Structural Alternation by Radial Keratotomy," *Journal of Biomechanical Engineering* 110:249-253 (Aug. 1988).

Johnson, Mark, et al., "Increased Corneal Thickness Simulating Elevated Intraocular Pressure," *Arch Ophthalmol* 96:664-665 (Apr. 1978).

Kwon, T.-H., et al., "Computational Simulation of Corneal Applanation," retrieved from www.asbweb.org/conferences/2004/pdf/278.pdf, 2 pages (2004).

Kwon, T.-H., et al., "Effect of Variations in Cornea Characteristics on Measured Intraocular Pressure," retrieved from www.asbweb.org/conferences/2004/pdf/285.pdf, 2 pages (2004).

Kwon, Tae-Hyun, "Minimally Invasive Characterization and Intraocular Pressure Measurement Via Numerical Simulation of Human Cornea," Doctoral dissertation, University of Illinois at Urbana-Champaign, cover page, pp. iii-xviii, 1-127 (2006).

Liou, Hwey-Lan, et al., "Anatomically accurate, finite model eye for optical modeling," *J. Opt. Soc. Am. A* 14(8):1684-1695 (Aug. 1997).

Orssengo, Girma J., et al., Determination of the True Intraocular Pressure and Modulus of Elasticity of the Human Cornea in vivo, *Bulletin of Mathematical Biology* 61:551-572 (1999).

Pinsky, Peter M., et al., "A Microstructurally-Based Finite Element Model of the Incised Human Cornea," *J. Biomechanics* 24(10):907-922 (1991).

Pinsky, Peter M., e al., "A Micro-Structurally Based Mechanical Model of the Human Cornea With Application to Keratotomy," *Invest Ophthalmol Vis Sci* 35(4):1296 (1994).

Skovoroda, Andrei R., et al., "Reconstructive Elasticity Imaging for Large Deformations," *IEEE Transactions on Ultrasonics, Ferroelectrics, and Frequency Control* 46(3):523-535 (May 1999).

Skovoroda, Andrei R., et al., "Theoretical Analysis and Verification of Ultrasound Displacement and Strain Imaging," *IEEE Transactions on Ultrasonics, Ferroelectrics, and Frequency Control* 41(3):302-313 (May 1994).

Whitacre, Marc M., et al., "The Effect of Corneal Thickness on Applanation Tonometry," *American Journal of Ophthalmology* 115:592-596 (May 1993).

\* cited by examiner

ACCURATE DETERMINATION OF INTRAOCULAR PRESSURE AND CHARACTERIZATION OF MECHANICAL PROPERTIES OF THE CORNEA

CROSS REFERENCE TO RELATED APPLICATION

This application claims the benefit of under 35 U.S.C. §119(e) of U.S. Provisional Application No. 60/951,260, filed Jul. 23, 2007, which is herein incorporated by reference.

TECHNICAL FIELD

The present disclosure relates to methods for accurate determination of intraocular pressure (IOP) and characterization of mechanical properties of the cornea in the eye, and also to use of a new mechanical probe for measurement.

BACKGROUND

Open-angle glaucoma arises from serious damage to the optic nerve and is strongly correlated with high intraocular pressure (IOP). High levels of IOP can lead to optic nerve damage, glaucoma, and eventually, blindness. Glaucoma is a very serious public health problem. This is exacerbated by the fact that in the vast majority of cases there are no early symptoms; by the time that loss of peripheral vision starts to become noticeable, irreversible damage to the optic nerve has already occurred. More than 2.2 million Americans age 40 plus are potentially at risk. (Friedman 2002). Indeed, an estimated three million people in the United States have the disease and as many as 120,000 are blind as a result. In addition, glaucoma is the number one cause of vision loss in African Americans, and Hispanics are also at higher risk of glaucoma.

Treatments to slow the progression of the disease are available. High IOP is the only significant modifiable risk factor. In fact, it has recently been rigorously established that lowering of IOP in individuals with glaucoma correlates with a delay in the onset of optic nerve damage and peripheral visual field loss. The same has also been recently established for a subset of patients with ocular hypertension, though this subset is not well characterized.

There are currently several instruments available for measuring IOP. The most widely used instrument is the Goldmann Applanation Tonometer (GAT), with the resulting readings of IOP being referred to as IOPG. Other instruments in use include the TonoPen and pneumo-tonometer (puff tonometer). It is widely known and generally accepted in the ophthalmology profession that these instruments have inherent systematic errors. These errors are generally attributed primarily to the effect of corneal stiffness which is unaccounted for in applanation tonometry.

Since IOP is used as the main screening mechanism for early detection of those at risk, it is evident that accurate measurement of IOP is of primary importance: false low IOP readings may delay or prevent necessary treatment, with devastating effects up to and including blindness; false high IOP readings may have undesirable consequences in the form of unnecessary and costly lifelong therapy. In light of this, it is clear that increased accuracy and reliability of IOP measurement has great public health value; indeed, the medical management of individuals at risk for glaucoma could be significantly enhanced.

Clinical studies have repeatedly shown that IOPG measurements with the GAT are influenced by the Central Corneal Thickness (CCT). Several authors have demonstrated the correlation between IOPG and CCT using data from simultaneous cannulation and applanation tonometry. The early study by Ehlers provided a table to recalculate IOPG taking account of the CCT of a patient. Ehlers, N., Bramsen, T., and Sperling, S., *Applanation Tonometry and Central Corneal Thickness*, Acta Ophthalmologica, 53(1), pp. 34-43 (1975). Many other references have also discussed the effect of CCT on IOP measurement.

On the other hand, data from clinical studies also shows considerable scatter in the correlation between IOPG and CCT. One implication of the observed scatter is that the true IOP, which is acknowledged to depend on corneal stiffness through CCT, also depends on the material or mechanical properties of the cornea. A correction which takes into account only the CCT, according to currently recommended practice, may not be sufficient.

BRIEF DESCRIPTION OF THE DRAWINGS

A more particular description of the disclosure briefly described above will be rendered by reference to the appended drawings. Understanding that these drawings only provide information concerning typical embodiments and are not therefore to be considered limiting of its scope, the disclosure will be described and explained with additional specificity and detail through the use of the accompanying drawings.

DETAILED DESCRIPTION OF PREFERRED EMBODIMENTS

The embodiments of this disclosure will be best understood by reference to the drawings, wherein like parts are designated by like numerals throughout. It will be readily understood that the components of the embodiments, as generally described and illustrated in the Figures herein, could be arranged and designed in a wide variety of different configurations. Thus, the following more detailed description of various embodiments, as represented in the Figures, is not intended to limit the scope of the disclosure, as claimed, but is merely representative of various embodiments. While the various aspects of the embodiments are presented in drawings, the drawings are not necessarily drawn to scale unless specifically indicated.

Figure 1A:
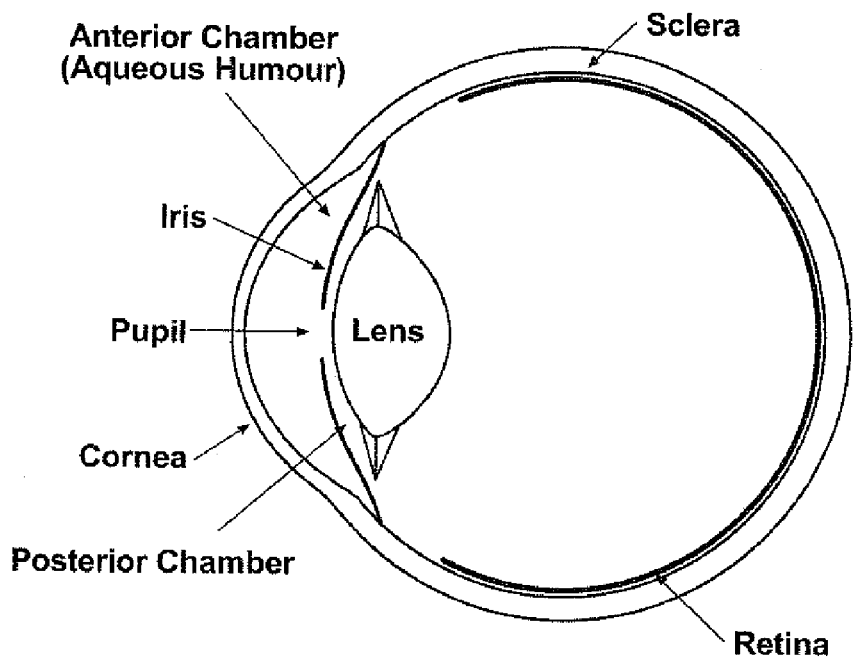
FIG. 1A is a diagram showing the structure of the human eye.

FIGS. 1A, 1B, and 3-4 are used to introduce the nonlinear finite element (FE) model of the human cornea, while FIG. 2 discusses measurement instruments (probes) used for producing measurement data of individual cornea. FIG. 1A is a diagram showing the structure of the human eye. The human eyeball is approximately spherical in shape measuring 24-25 mm in diameter. The main function of the eyeball is to provide protection and an optimum environment for the retina. All of the other complex structures of the eye are dedicated to the accurate and efficient functioning of the retina.

The fluid-filled space behind the iris and in front of the lens is called the posterior chamber; the sclera is an opaque, white, and resilient outer coat of the eye which covers the posterior five-sixths of the globe. The anterior chamber is an elliptical space between the iris and the cornea; it acts as a reservoir for the aqueous humour. The aqueous humour is the fluid that fills the chambers. One-sixth of the globe consists of a uniquely transparent, bulged forward, fibrous structure called the cornea, which is responsible for approximately two-thirds of the eye's focusing power. This is the reason why most refractive surgeries are associated with the cornea.

Figure 1B:
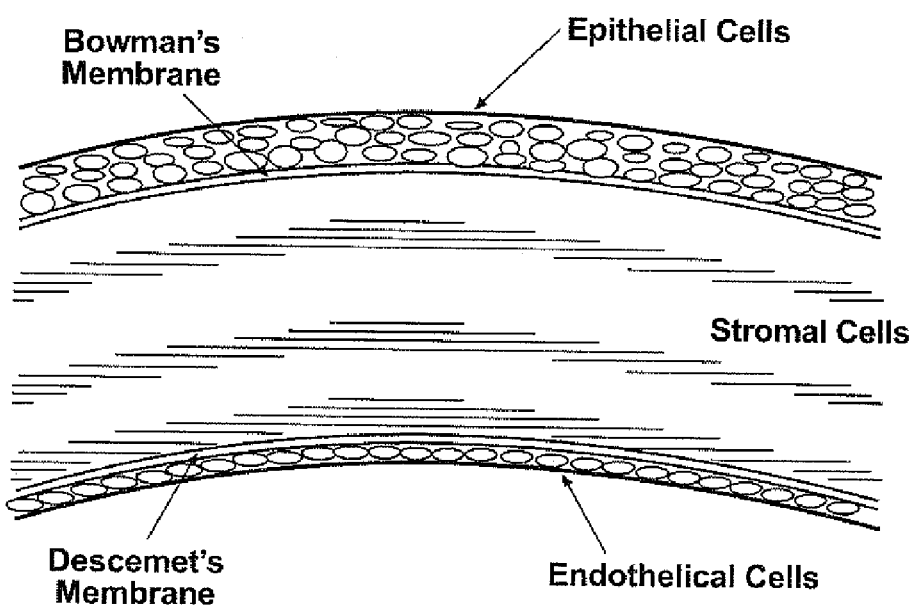
FIG. 1B is a diagram showing the five distinct layers of the cornea.

FIG. 1B is a diagram showing the five distinct layers of the cornea. The adult cornea is only about 0.5 mm thick and is composed of 5 layers: epithelium, Bowman's membrane, stroma, Descemet's membrane, and endothelium. The cornea has a complex, lamellar microstructure. The stroma, the middle (and thickest) layer of the five distinct layers constituting the cornea, consists of perhaps 200-300 lamellae parallel to the surface of the cornea, which are composed primarily of collagen fibrils embedded in a matrix rich in proteoglycans. Within a lamina, the collagen fibrils are essentially parallel, but adjacent laminae generally do not have the same orientation.

Within the cornea, the laminae are organized predominantly in superior-inferior and nasal-temporal directions, whereas in the sclera the collagen fibrils are organized primarily circumferentially. At the limbus, or the margin where the cornea meets the sclera, the corneal fibril families appear to curve over a short distance to blend into the circumferential scleral fibrils. These preferred directions are more pronounced in the posterior than in the anterior stroma. In the anterior portion of the stroma (100-120 μm, approximately, of a total thickness of 520-530 μm in a normal eye), the fibrils undulate in the thickness direction, and regions of amorphous extracellular matrix are interspersed between the fibrils. This provides additional interlaminar strength and stiffness compared to the posterior portion where there is little interlayer weaving. Because of this micro-structure, the cornea is mechanically neither isotropic nor homogeneous; idealizations of its mechanical behavior in response to applanation or indentation must take account of this fact.

Measurement of the mechanical constitutive properties of the cornea is extremely difficult because of its complex microstructure. In fact, it is fair to say that the elastic properties of the cornea have never been fully characterized. Several standard types of tests have been utilized ex vivo: (1) Diametral strips or circular ring specimens, excised from the cornea, stretched uniaxially or radially, respectively, (2) membrane inflation of the intact cornea mounted in a testing frame, and (3) ocular rigidity tests in which the anterior chamber is cannulated and fluid is introduced under increasing pressure to determine a pressure versus volume change relationship. There are many technical difficulties associated with performing these tests, not the least of which is post-mortem physiological changes which undoubtedly alter the mechanical characteristics of the cornea. In addition, these tests are essentially one-dimensional. Therefore, they cannot provide enough information to characterize the non-linear anisotropic properties of the cornea.

Recently, high frequency ultrasound has been proposed for extracting information about the elastic properties of corneal tissue in vivo. Current methods for determining elastic constants from the ultrasound data assume linear, incompressible and isotropic elastic behavior. Extension of these methods to fully characterize the nonlinear anisotropic behavior of the cornea will apparently be quite difficult.

Simplified analytical models and more detailed numerical finite element (FE) models have been employed to study the effects of refractive surgery on the cornea, primarily radial keratotomy (RK). Corneal indentation or applanation has also been studied using simplified analytical models, and FE models. These research studies have provided insight into the general characteristics of the biomechanical response of the cornea. However, they cannot address the individualized assessment of corneal bending resistance to indentation or applanation because they do not incorporate a means of determining the elastic properties of the individual cornea.

Because of the complex structure of the human cornea as discussed above, its mechanical properties are necessarily complex. The human cornea is highly inhomogeneous, anisotropic, and nonlinear. Currently, there are no methods available for in vivo determination of its mechanical properties. Accurate and reliable determination of intraocular pressure (IOP), however, should also account for the effect of the mechanical properties of the cornea on its stiffness. What is clearly required in order to accurately evaluate corneal bending resistance during tonometry is in vivo characterization of specific, individual corneas.

Figure 2A:
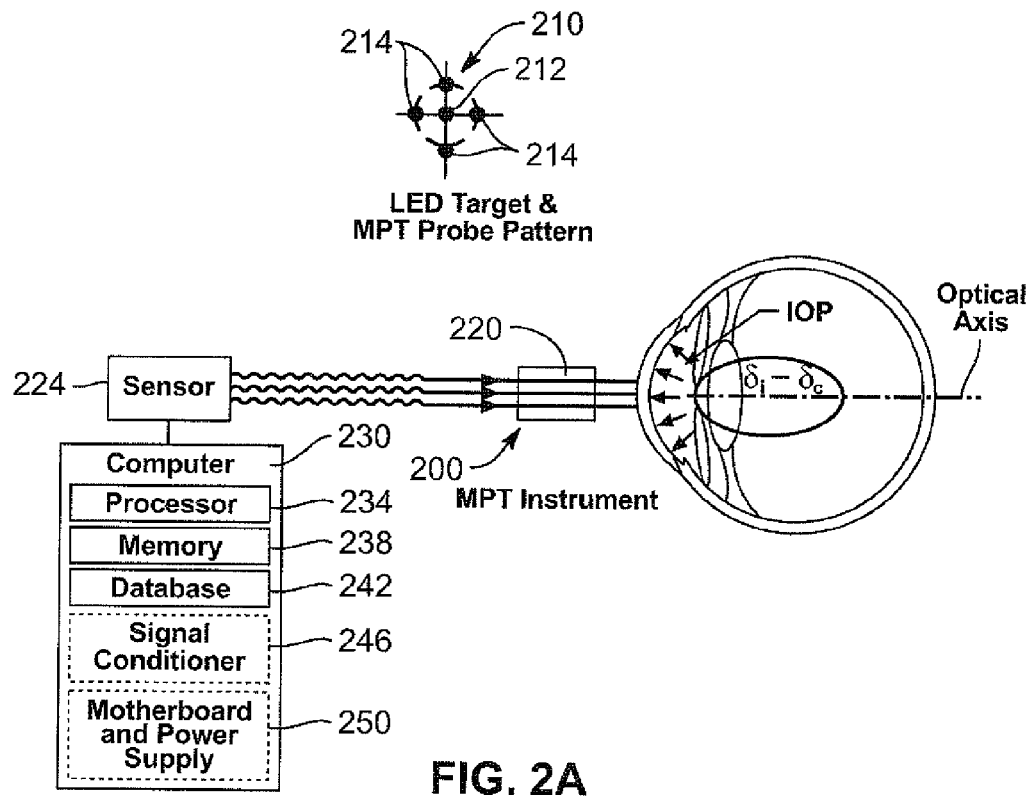
FIGS. 2A and 2B are, respectively, a diagram of a multiple probe tonometer (MPT) as used to gather observational data, in vivo, from individual cornea, and a graph of MPT probe force versus probe deflection.
Figure 2B:
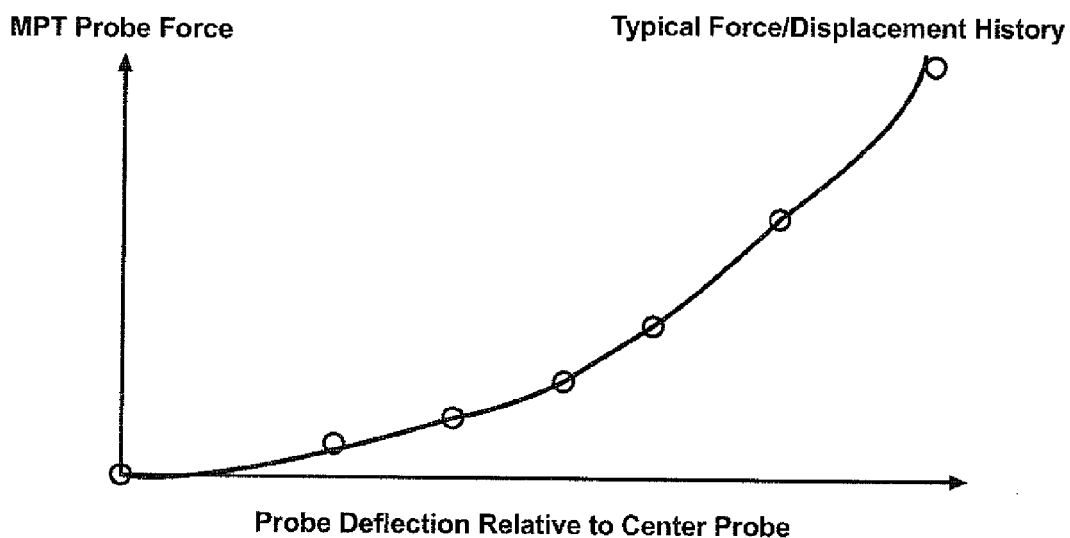

FIGS. 2A and 2B are, respectively, a diagram of a multiple probe tonometer (MPT) 200 as used to gather observational data, in vivo, from individual cornea, and a graph of MPT probe force versus probe deflection. Other instruments using a single probe or varying numbers of probes are also envisioned, and therefore, the number of probes is not a critical factor. These various measurement instruments will hereinafter be variably referred to as "probe tonometers" 200. For instance, in one embodiment, a probe tonometer 200 may be designed as a modified version of the widely used Goldmann Applanation Tonometer (GAT) to fulfill the same or similar function as the MPT as disclosed herein. This disclosure, however, differs from GAT in that it produces a simultaneous record of force versus displacement of the cornea, and does not rely on the application of an applanation principle (flattening of the central portion of the cornea), which in the GAT requires an associated optical procedure.

As shown in FIG. 2A, probe tonometers 200, including the MPT 200, provide probe force histories and cornea deflections at the probe location (or locations) relative to the cornea central deflection throughout the tonometry process. To so provide, probe tonometers 200 gradually apply a very small force to the corneal surface and simultaneously record both the force that is applied and the resulting displacement (indentation) of the cornea.

For example, the hand-held MPT 200 displayed in FIG. 2A employs five parallel probes: one central probe 212 and 4 additional probes 214 arranged in a circular pattern (approximately 5 mm diameter) outside the optical zone. The probes 212, 214 are mounted in a stainless steel clamping collar 220 as illustrated in FIG. 2A. Each probe 212, 214 is a Micro-gauging Differential Variable Reluctance Transducer (DVRT) (such as manufactured by Microstrain, Inc. of Williston Vt.), including a spring-loaded Nitinol central core that can slide inside an about 1.8 mm diameter stainless steel sleeve. The central probe 212 is slightly recessed with respect to the peripheral probes 214 to approximately compensate for corneal curvature.

During tonometry, the position of a core with respect to its sleeve, and thus its spring compression, is accurately measured with a sensor 224, from which the probe force is directly determined using the known spring rate. Several probe tip styles (not shown) are available. The sensor 224, in turn, is coupled with a computer 230 having a processor 234, a memory 238, and a database 242. Herein, the phrase "coupled with" is defined to mean directly connected to or indirectly connected through one or more intermediate components. The processor 234 receives and processes measurement data, which is stored in the memory 238 and/or database 242.

A stationary light emitting diode (LED) grid is projected onto the cornea from a light source to provide a cross-hair target with reticles to guide the MPT operator. The MPT 200 is manually advanced as a unit to indent the cornea, using this target, and core positions with respect to their respective sleeves are continuously monitored and recorded by the computer 230. In a prototype MPT 200, each DVRT is cable or wirelessly connected to an individual DEMOD1 (Microstrain, Inc.) printed circuit card (PCB) for signal conditioning 246, and installed in an 8-channel smart motherboard/power supply unit 250, which is directly connected to the computer 230 on which the computational algorithms are carried out by the processor 234. The signal conditioner 246 and motherboard/power supply unit 250 may optionally be integrated with the computer 230, indicated by the dashed lines. From the measured information, the processor 234 determines the forces in all probes which are in contact with their respective targets, as well as the corresponding deflections of the cornea, relative to the deflection of the central target point. The data from these measurements will allow for more accurate characterization of the physical properties of the cornea, and therefore, more accurate IOP measurement.

The computational method underlying this disclosure differs from other computational simulations in that it integrates actual physical measurement and computational simulation. Computer-based self-learning algorithms that utilize the above-referenced force versus displacement data may be used to accurately determine IOP and the mechanical properties of the cornea (discussed later with reference to FIGS. 17 through 20). A non-invasive method is proposed for accurate in vivo measurement of IOP that also determines the material properties of the cornea. This method can be used to measure Central Corneal Thickness (CCT) if desired, although methods already exist to do so.

One proposed method is a simulation-based computational tool that uses the history of the applanating force and the corresponding displacement of the applanator. This method requires a probe tonometer as disclosed with reference to FIG. 2A, or a modified Goldmann-type (GAT) tonometer, either of which can measure and record the applanating force and displacement histories. A genetic algorithm (GA) is used to match the measured force-displacement history from the modified GAT with a finite element (FE) simulation of the applanation tonometry.

Direct application of the GA methodology requires a large number of nonlinear FE simulations to be carried out that would considerably slow the application of the proposed method. Because speed is an important practical consideration in clinical applications, the FE simulations are effectively carried out using a trained neural network (NN). It is demonstrated that the combination of the genetic algorithm (GA) and a trained NN are computationally very efficient; results can be obtained within one or two minutes on current (2007) desktop computers.

The development and evaluation of the proposed method is carried out using synthetic applanator target data generated by an FE simulation. There are two reasons for adopting this approach. First, in the development and evaluation stage, it provides a means for evaluating accuracy, because the "answer" is known. Second, the modified applanator instrument described above with reference to FIG. 2A, which is needed to provide the target data, did not exist during the experiments described herein.

The proposed method is first examined using population average corneal dimensions and properties. Then, the robustness of the proposed method is examined by performing a parametric study using corneas with a range of dimensions and properties. Finally, a well-known clinical case of a 17-year-old woman reported by Johnson was studied. Johnson, M., Kass, M. A., Moses, R. A., and Grodzki, W. J., *Increased Cornea Thickness Simulating Elevated Intraocular Pressure*, Arch. Ophthalmol., 96(4), pp. 664-665 (1978). Her GAT readings were consistently very high (30-40 mmHg) but her actual IOP was later revealed by cannulation to be only 11 mmHg. The results of the comparison demonstrate that the proposed method is capable of providing accurate IOP measurements even in a difficult and extreme case.

An accurate finite element (FE) model of the human cornea, including the effect of the aqueous humour in the anterior chamber, is needed for the proposed method. The nonlinear finite element model used in this study is briefly described herein. The axisymmetric (but aspherical) geometries of the anterior and posterior surfaces of the cornea in the FE model are expressed by the following equation:

$$r^2+(1+Q)z^2-2zR=0 \quad (1)$$

where the origin is on the (anterior or posterior) surface of the cornea at the optical axis, the z axis points inward along the optical axis, and r is the radial distance from the optical axis. Q is an asphericity parameter (Q=0 for a spherical surface) and R is the radius of curvature at the apex of the cornea. A value of Q<0 corresponds to a prolate ellipsoidal shape, and Q>0 corresponds to an oblate ellipsoidal shape. Suggested average values of the parameters are listed in Table 1.

TABLE 1

Geometry Parameters of the Cornea:

| Surface | Radius of Curvature, R (mm) | Asphericity, Q |
|---|---|---|
| Anterior | 7.77 | −0.18 |
| Posterior | 6.40 | −0.60 |

When the two surfaces are separated lay a distance of 500 μm (the population average CCT) at the corneal (or optical) axis they are separated by a distance of 910 μm at a radius of 6 mm from the center. Thus, the corneal thickness gradually increases from its center to its periphery. Once the anterior and posterior surfaces are defined, the aspherical FE model of the cornea is developed using 4-noded axisymmetric solid elements.

A material model of the cornea is explained next. The cornea has a complex lamellar microstructure; for simplicity, it is modeled as a nonlinear transversely isotropic homogeneous material herein. The constitutive model is developed starting from Fung's exponential strain energy function:

$$W = \frac{1}{2\alpha}(e^\Phi - 1), \text{ where } \Phi = \alpha\varepsilon^T D_0 \varepsilon, \quad (2)$$

and where W is the strain energy density and ε is the (Green) strain vector. Fung, Y. C., Fronek, K., and Patitucci, P., *Pseudoelasticity of Arteries and the Choice of Its Mathematical Expression*, J. Opt. Soc. Am., 237(5), pp. H620-H631 (1979). The parameter α determines the degree of non-linearity (higher values of α correspond to greater degrees of nonlinearity) and $D_0$ is the (linear) elastic tangent stiffness matrix at zero strain. The secant stiffness $D_s$, obtained as usual by differentiating the strain energy function with respect to the strain vector, is simply $$D_s = e^\Phi D_0. \quad (3)$$

A second differentiation yields the Jacobian (tangent stiffness) matrix Dt:

$$D_t = e^\Phi [D_0 + 2\alpha D_0 \varepsilon \varepsilon^T D_0]. \quad (4)$$

The initial tangent stiffness matrix Do contains five independent elastic constants for transverse isotropy. These can be reduced to a single independent elastic constant $E_p$ (the Young's modulus in the plane of isotropy) by using correlations proposed for the human cornea by Bryant et al. Bryant, R. B. and McDonnell, P. J., *Constitutive Laws for Biomechanical Modeling of Refractive Surgery*, J. Biomech., 118 (4), pp. 473-481 (1996).

Figure 3:
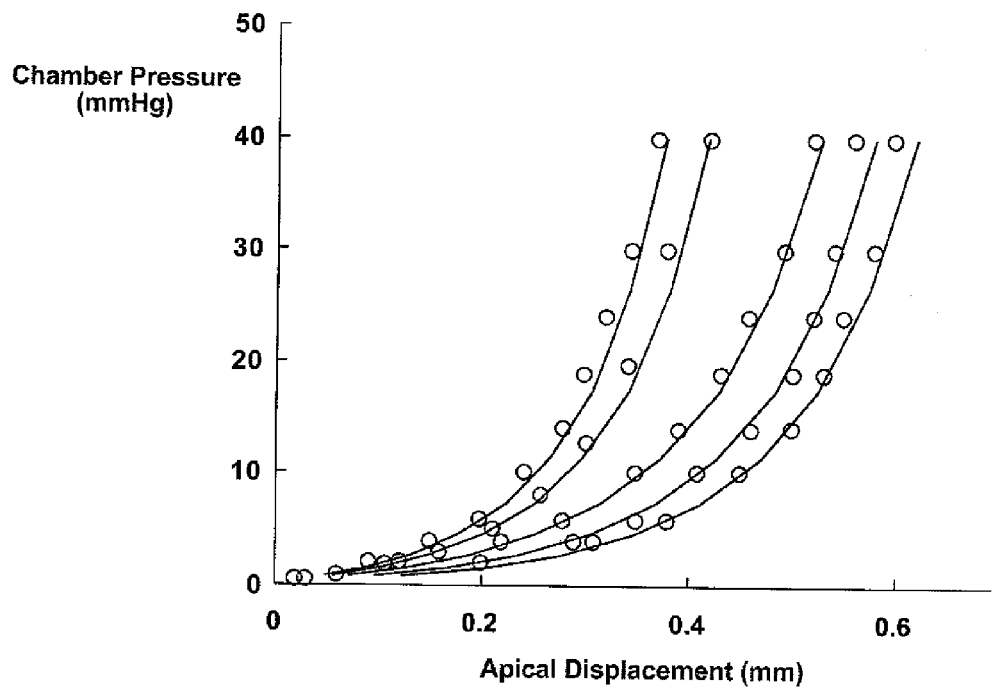
FIG. 3 is graph showing the calibration of a nonlinear material model in finite element (FE) simulations (circles) with the experimental results (lines) by Bryant et al. (1996) varying as per apical displacement of the cornea.

FIG. 3 is graph showing the calibration of a nonlinear material model in finite element (FE) simulations (circles) with the experimental results (lines) by Bryant et al. varying as per apical displacement of the cornea. Id. Using Bryant's correlations, the in-plane Young's modulus $E_p$ and the non-linearity parameter α are determined by calibration with experimental data obtained by Bryant from twelve excised human eye-bank corneas. In Bryant's in vitro inflation tests, each cornea in turn was mounted on an artificial anterior chamber and its apical displacement was measured during incremental pressure increases. Corneal thickness remained stable, ranging from about 401 μm to about 404 μm during the tests.

Calibrated finite element (FE) results are shown in FIG. 3 and compared with the experimental results for five corneas. Note that there are substantial variations between the inflation responses of the different individual corneas. Calibrated values of $E_p$ ranged from 0.12 to 0.35 MPa for the 5 tests; calibrated values of a ranged from 417 to 1000 (1/MPa). The results also showed that the nonlinearity parameter a can be related to $E_p$ with sufficient accuracy by a linear interpolation function. This nonlinear material model, with one material parameter $E_p$, was implemented in the user-defined routine (UMAT) in the general purpose finite element program ABAQUS. A more general version of the nonlinear material model, with six independent material parameters (five elastic constants plus the nonlinearity parameter α) was also implemented in UMAT.

The interaction between the aqueous humour and cornea is included by modeling the fluid-filled anterior chamber with hydrostatic fluid elements. The aqueous humour elements of the anterior chamber are assumed to be incompressible with fluid mass of 100 kg/m³. These elements provide the coupling between the deformation of the cornea and the pressure exerted by the aqueous humour on the anterior surface of the cornea.

The initial stress on the cornea is due to IOP. It is assumed that Equation (1) describes the deformed corneal geometry under the influence of the pre-existing IOP. Because the initial undeformed geometry of the cornea is unknown, a two step procedure is used to model the initial insitu state of stress in the cornea subjected to IOP, prior to applanation. In the first step of the computational procedure, the initial linear stiffness of the cornea is artificially increased by a suitable factor (a factor of 100 is used, but other factors may be deemed suitable through experimentation) and the intraocular pressure is applied in order to determine a set of insitu stresses in the cornea which equilibrate the IOP, without producing appreciable deformations. The deformed shape of the cornea at the end of the first computational step is therefore very close to that described by Equation (1) as desired. Then, the strains that would be consistent with the insitu stresses in the actual constitutive model are determined at each material reference point via an iterative (Newton-Raphson) numerical process and used in the next step as the initial state of strain. Applanation tonometry is modeled in the second step with the actual corneal constitutive model properties and the initial strains determined from the first step.

Figure 4:
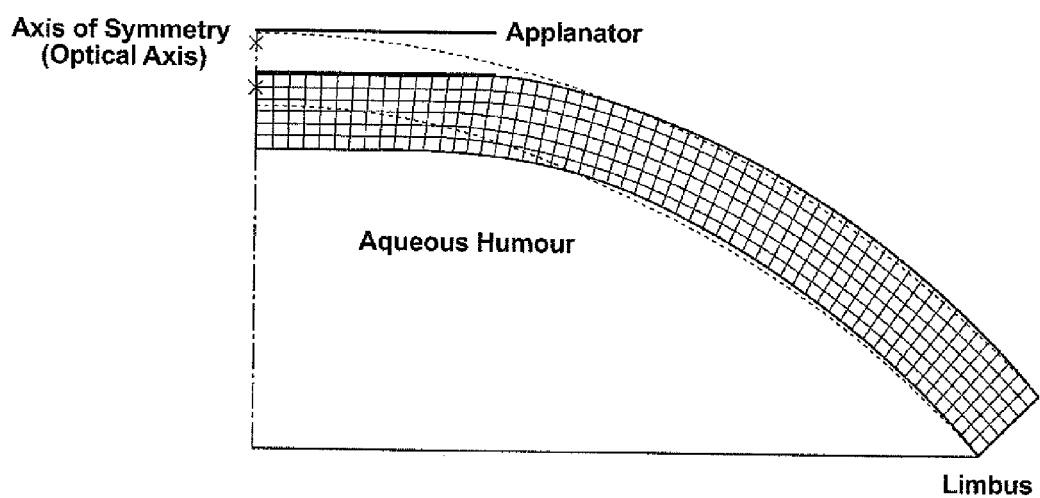
FIG. 4 is a graph showing a cross-sectional view of the deformed shape of an applanated cornea having superimposed thereon an undeformed shape. The central corneal thickness (CCT) is 550 µm, $E_p$ (the Young's modulus in the plane of isotropy) is 0.23 MPa, and intraocular pressure (IOPT) is 16 mmHg.

FIG. 4 is a graph showing a cross-sectional view of the final deformed shape of an applanated cornea having superimposed thereon an undeformed shape. The central corneal thickness (CCT) is 550 μm, $E_p$ is 0.23 MPa, and intraocular pressure (IOPT) is 16 mmHg. The applanation procedure was simulated by contact analysis with a rigid surface representing the applanator. Additional details of modeling procedure can be found in Kwon and Kwon et al.

A method of analysis for determining IOP is now explained.

Figure 5:
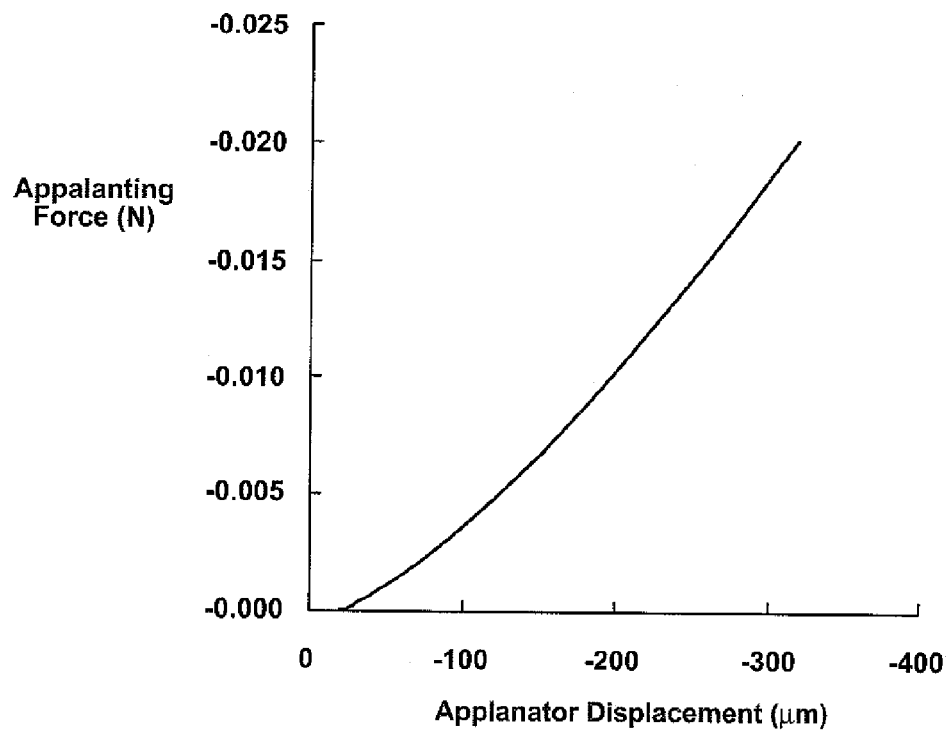
FIG. 5 is a graph showing a response curve from simulated Goldman Applanation tonometry (GAT), in which CCT is 550 µm, $E_p$ is 0.23 MPa, and IOPT is 16 mmHg.

FIG. 5 is a graph showing a typical response curve from simulated Goldmann Applanation tonometry (GAT), in which CCT is 550 μm, $E_p$ is 0.23 MPa, and IOPT is 16 mmHg. The GAT in current use measures only the applanation force corresponding to the final applanated area, not the applanation displacement nor the histories of force and displacement. Knowledge of only the final applanating force is not sufficient information for application of the proposed method; it requires the histories of applanating force and displacement (FIG. 2B), which can be provided through a probe tonometer (or MPT) 200 (FIG. 2A). As the data gathered herein did not use such a probe tonometer, in lieu of actual clinical applanation response data, target response data may be constructed via FE simulation, as discussed herein.

The problem of determining IOP and material properties can be viewed as an inverse problem, albeit of a very difficult type, with a known output, i.e. the force-displacement response shown in FIG. 5. The particular difficulty arises because the IOP produces a preexisting state of initial stress in the cornea, for which there is no independent response data. This inverse problem is solved herein by searching for an IOP which produces the target response of the cornea under applanation. A genetic algorithm (GA) is proposed for use as an appropriate tool to solve this problem.

The genetic algorithm (GA) is a computational model loosely based on natural evolution. In its simple form, it has all the necessary characteristics for optimization problems. In the GA, a problem to be optimized is represented by a string which encodes the variables of the problem. Each variable is encoded in binary bits and all binary bits are concatenated together to form a binary string which encodes the entire set of variables. A population of strings is randomly initialized at the beginning. Evolutionary pressure, however, leads to fitter individuals in the population and moves the fitter individuals in the population closer to satisfying the fitness functions of the problem.

Use of GAs combined with FE simulation of GAT is now explained.

Figure 6:
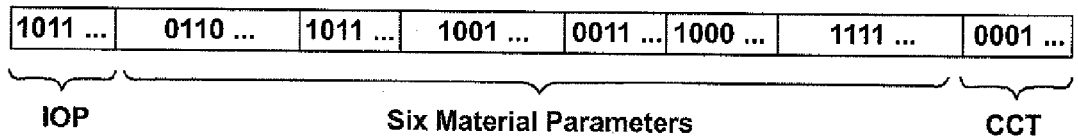
FIG. 6 is a graph showing encoded variables in the genetic algorithm (GA) strings.

FIG. 6 is a graph showing encoded variables in the genetic algorithm (GA) strings. The objective of the GA application is to minimize the difference between the response curve obtained from GAT and the (target) simulated response from the FE model of the cornea and aqueous humour. The members of the population in the GA are binary strings that represent the variables of the problem, i.e. the parameters that define the FE model of the cornea and aqueous humour. The Variables encoded in the GA strings are: IOP; constitutive material model parameters of the cornea ($E_p$ is especially considered in this case); and CCT.

The fitness function to be maximized is the inverse of the difference between the applanator displacements from the FE simulation and the target applanator displacements generated by the masked FE simulation. The fitness function is shown in Equation (5), below, where N is the number of discrete points on the applanator response curve.

$$F = \frac{1}{1 + \sum_{i=1}^{N} \frac{|IndividualResponse_i - TargetResponse_i|}{|TargetResponse_i|}} \quad (5)$$

The target applanation response curve in FIG. 5 corresponds to a population average cornea with CCT of 550 μm, an $E_p$ of 0.23 MPa, and IOPT of 16 mmHg. This provides the synthetic GAT target response to illustrate the performance of the GA. Table 2 summarizes the control parameters used in the GA. In this example it is assumed that CCT has been independently measured by other means (e.g., ultrasound) and is therefore known.

TABLE 2

GA Control Parameters with Two Genes, $E_p$ and IOPT

| | |
|---|---|
| String Length (bits) | 97 |
| Crossover Rate | 1.0 |
| Mutation Rate | 0.01 |
| Population Size | 50 |
| Number of Generations | 50 |

Figure 7:
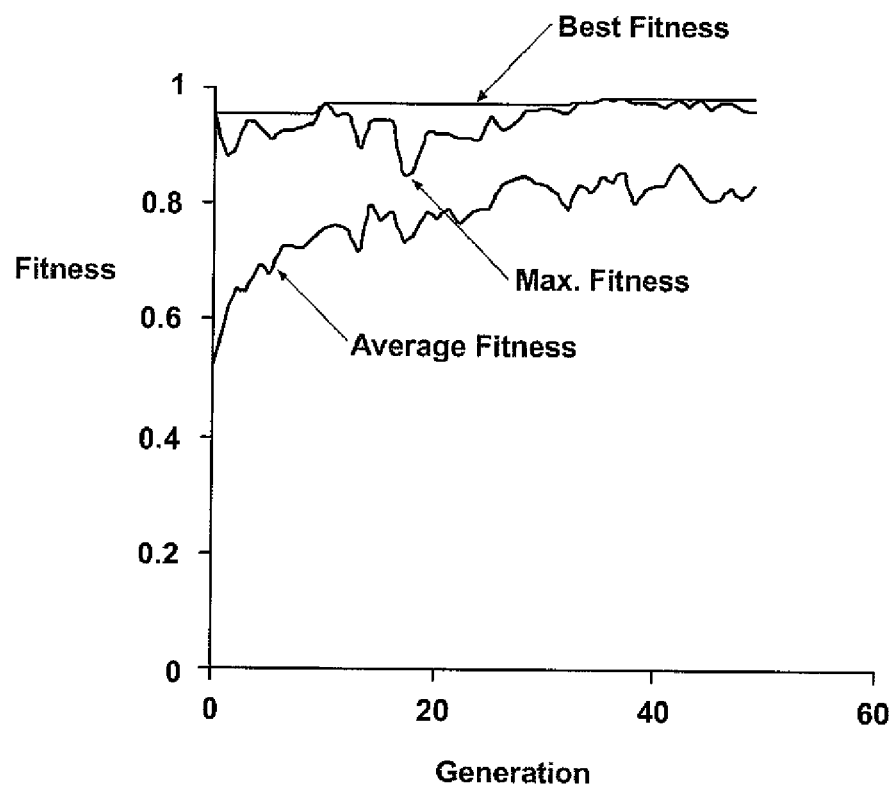
FIG. 7 is a graph showing the best, maximum, and average fitnesses during GA evolution.

FIG. 7 is a graph showing the best, maximum, and average fitnesses during GA evolution. The strings in the initial population are randomly selected from the range of variables shown in Table 3. The variables are assumed to be uncorrelated, but may have some relation. The "average fitness" is defined as the average value in the current generation. The "maximum fitness" is defined as the largest fitness value in the current generation. The "best fitness" is defined as the largest fitness value over all generations, up to and including the current generation.

TABLE 3

Random Selection of Genes for Initial Population

| Genes | Range | Target |
|---|---|---|
| $E_p$ (MPa) | 0.1~0.4 | 0.23 |
| $E_t$ (MPa) | 0.01~0.04 | 0.023 |
| $v_{pt}$ | 0~0.5 | 0.5 |
| $v_p$ | 0~0.5 | 0.5 |
| $G_t$ (MPa) | 0.00476~0.019 | 0.0109 |
| α (1/MPa) | 283.13~1056.26 | 618.15 |
| IOP (mmHg) | 7~25 | 16 |

The IOP prediction from the fittest ("best fitness") individual is 15.7 mmHg which is a reasonable approximation of the true (target) IOP (16.0 mmHg). Additional GA runs were made with two additional synthetic targets. Table 4 shows the GA results from these additional GA runs. It can be seen that the GA accurately predicts IOP while the GAT simulation overestimates the true IOP for the thicker CCTs, as expected.

TABLE 4

IOP and $E_p$ Predictions from GA Runs for Best Fitness Individual:

| Case | Target variables | | GAT simulation | GA prediction |
|---|---|---|---|---|
| CCT 530 μm | IOP: 16.0 mmHg 0.23 MPa | $E_p$: | IOPG: 16.0 mmHg $E_p$: — | IOP: 15.7 mmHg $E_p$: 0.28 MPa |
| CCT 650 μm | IOP: 16.0 mmHg 0.28 MPa | $E_p$: | IOPG: 21.5 mmHg $E_p$: — | IOP: 16.4 mmHg $E_p$: 0.28 MPa |
| CCT 900 μm | IOP: 11.0 mmHg 0.23 MPa | $E_p$: | IOPG: 18.3 mmHg $E_p$: — | IOP: 11.9 mmHg $E_p$: 0.26 MPa |

Neural networks (NN) may represent FE simulations of GAT.

Figure 8:
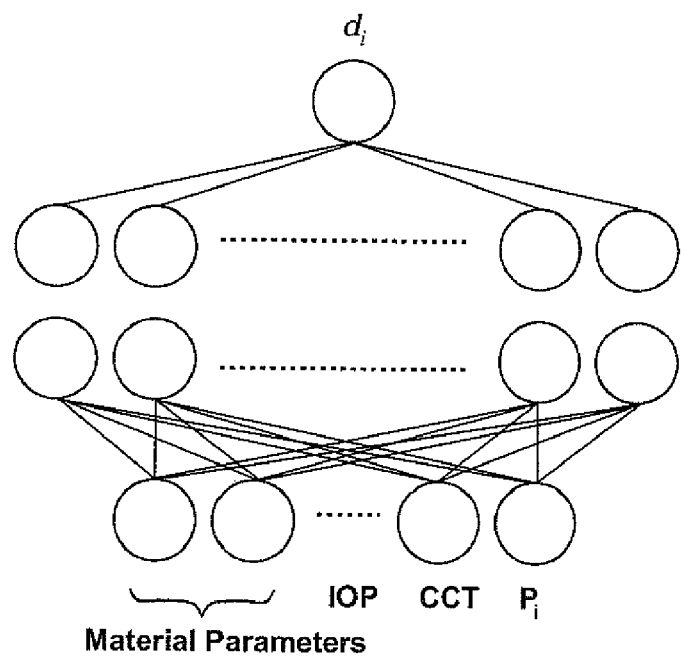
FIG. 8 is a diagram showing architecture of a neural network used to replace FE simulation of GAT.

FIG. 8 is a diagram showing architecture of a neural network (NN) used to replace FE simulation of GAT. A drawback in the application of GA is the large number of function evaluations required to determine the fitness of each member of the population at each generation. In this problem each function evaluation requires a nonlinear FE simulation of GAT. For a GA run with a population of 50 over 50 generations, 2500 FE simulations of GAT are needed. With an average computational time of three minutes per FE simulation, each GA run would take 7500 minutes to complete. This is clearly not feasible, especially in a clinical setting, and may be remedied by replacing the FE simulations of the GAT with a trained neural network (NN). The structure of the neural network which is trained to learn the response from an FE GAT simulation is shown in FIG. 8.

The input layer contains six material parameters, CCT, IOPT, and the value of the applanating force $p_i$ at a particular stage "i" in the applanation. The single output $d_i$ of the neural network represents the value of the corresponding applanator displacement.

A large number of FE simulations of GAT are first performed to generate the training data for the NN. For each GAT simulation, the material parameters, CCT, and IOPT are selected randomly within chosen, predetermined ranges of these variables ($E_p$ 0.07-0.45 MPa, CCT 400-950 μm, IOPT 7-30 mmHg). From each GAT simulation, pairs of ($p_i$, $d_i$) are obtained from the applanation response curve. The procedure for generating the NN training data is shown in FIG. 9.

Figure 9:
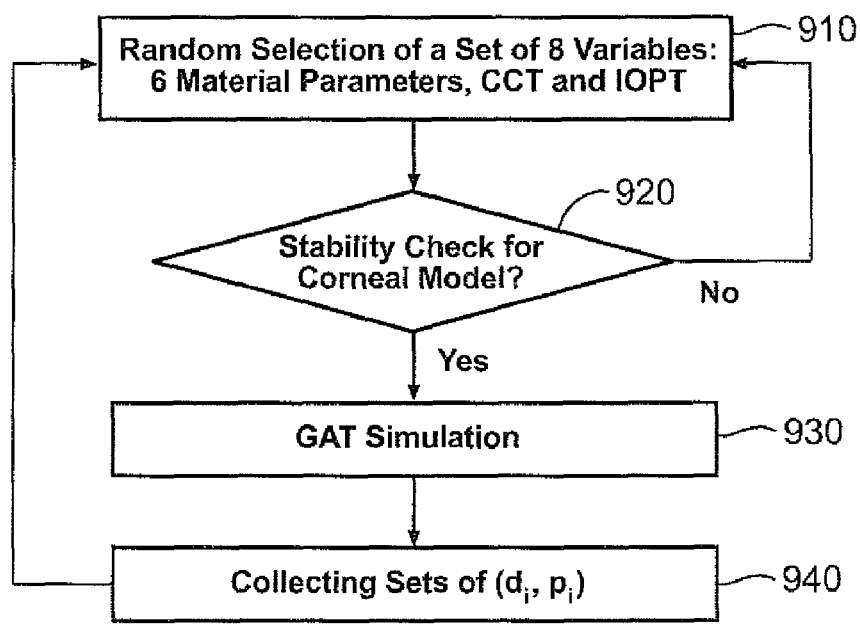
FIG. 9 is a flow chart of neural network (NN) training data for representing FE simulation of GAT.

FIG. 9 is a flow chart of neural network (NN) training data for representing FE simulation of GAT. At block 910, eight variables are randomly selected that include 6 material parameter, central corneal thickness (CCT), and intraocular pressures (IOPT). At block, 920, a stability check is performed for the corneal model. If it is stable, the NN training continues; if not, the flow chart returns to block 910. At block 930, GAT simulation is performed. At block 940, sets of ($d_i$, $p_i$) are collected. After block 940, the training is iteratively performed by returning to block 910. Not all randomly selected sets of material parameters are valid on physical grounds, i.e., the six material parameters must satisfy an inequality that guarantees that the initial tangent stiffness matrix is positive definite. Of the 1000 randomly selected sets of material parameters, 964 passed this material stability check, and FE simulations of GAT were carried out for these cases.

The neural network was trained using the "Rprop" back-propagation algorithm [36]. An additional 200 cases ("test cases") were generated in the same manner to test the NN performance on cases which were not members of the training set.

Figure 10:
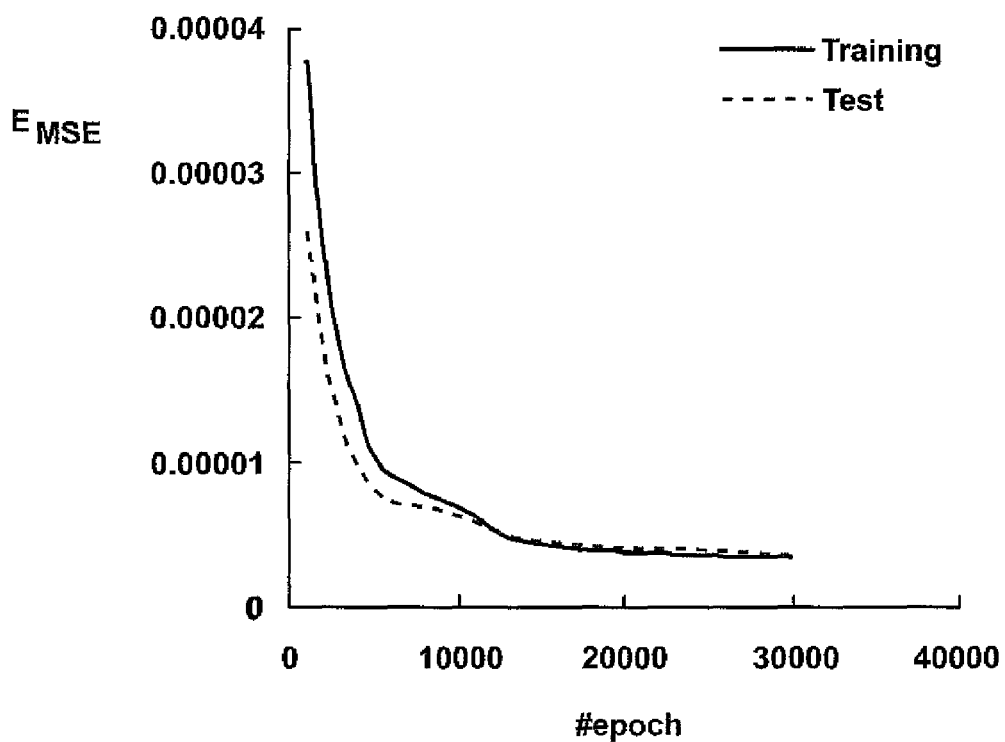
FIG. 10 is a graph showing a summary of the training and testing of neural networks to replace FE GAT simulation.

FIG. 10 is a graph showing a summary of the training and testing of neural networks (NNs) to replace FE GAT or probe tonometer simulation. The horizontal axis is the number of epochs, or iterations, used to train the NN and the vertical axis is the mean-squared-error. During iterative training of a neural network, an epoch is a single pass through the training data. The error function $E_{MSE}$, where MSE is "mean-squared-error," plotted along the y-axis displays the differences between the NN and target outputs. The mean-squared-error normalizes the sum of squared errors with the number of training cases. At each epoch, $E_{MSE}$ is calculated from training cases (solid line) and test cases (dashed line) respectively. FIG. 10 shows that the NN converges quickly during training. The trained NN is then used for fitness evaluations within the GA, in lieu of the much more computationally expensive FE simulations.

Genetic algorithms may use neural network (NN) representations of GAT. To investigate the performance of the GA with incorporated NN, the applanation response shown in FIG. 5 (CCT=550 μm, Ep=0.23 MPa, IOPT=16 mmHg) is once again used as the target response. The control parameters are again as shown in Table 2, except that the number of generations is increased to 500. Table 3 shows the range of variables for the initial population. The total computational time for each GA run with a population of 50 for 500 generations is less than 3 minutes on a typical desktop computer (2007). The GA results are for the best fitness individual. Normally, in any application of GA, multiple runs are performed; the results will usually differ due to the fact that each run starts from a completely random initial population. In this example, five GA runs were performed. The results are shown in Table 5.

TABLE 5

Best Fitness from Five GA Runs:

| | Run No. | | | | | Average |
|---|---|---|---|---|---|---|
| | #1 | #2 | #3 | #4 | #5 | (S.D./Average) |
| Computed IOP (mmHG) | 16.0 | 15.1 | 15.7 | 15.3 | 17.6 | 16.0 (0.06) |

Figure 11:
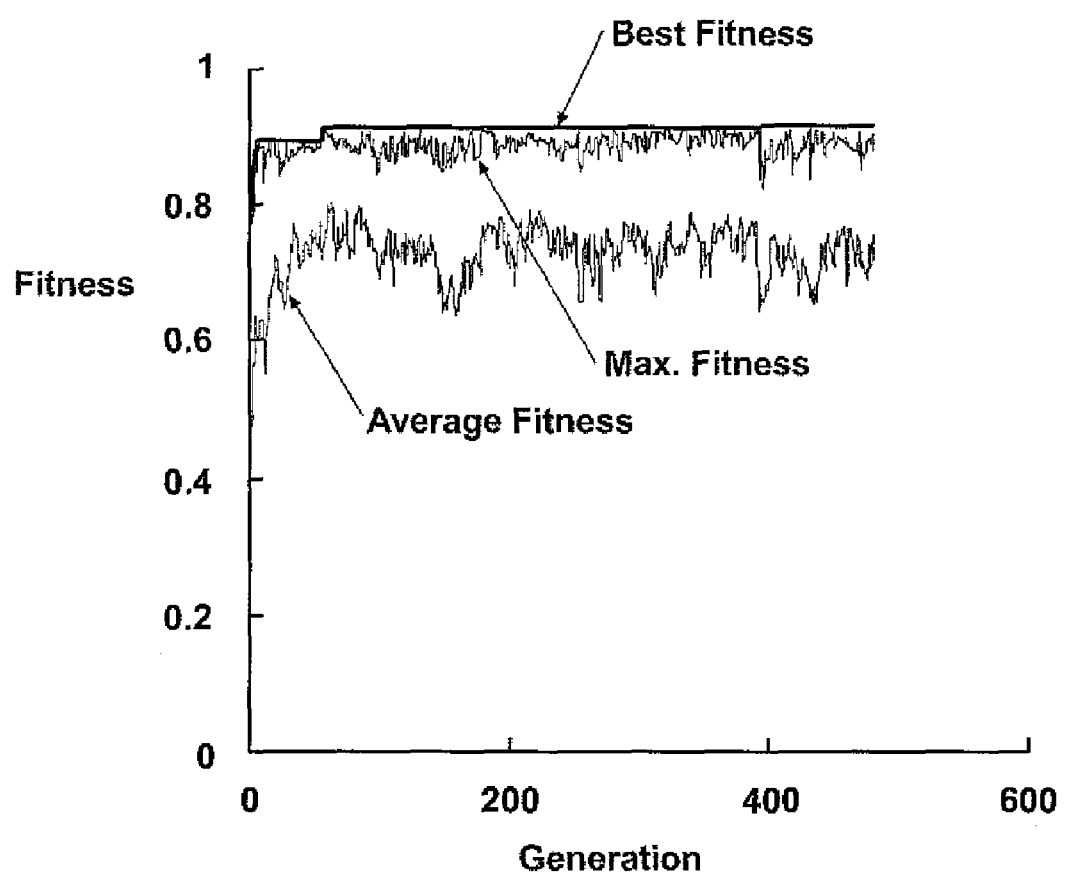
FIG. 11 is a graph showing the best, maximum, and average fitnesses for GA and neural networks (NN) during evolution.

FIG. 11 is a graph showing the best, maximum, and average fitnesses for GA and neural networks (NNs) during evolution for one of the five GA runs just described. The results of all of the five GA runs are reasonable approximations of the true IOP (16 mmHg) as seen in FIG. 11.

To study the effect of variations in the primary variables (CCT and IOPT) on the performance of the proposed GA/NN method, a limited parametric study was conducted. Three values each of CCT and IOPT were selected, resulting in a total of nine cases. A synthetic GAT was first generated by FE simulation for each of the nine cases to provide target applanator responses. The corresponding IOPG values computed from these FE GAT simulations are shown in Table 6. As expected, the IOPG values underestimate the corresponding IOPT values for thin corneas and overestimate them for thick corneas. This observation is consistent with the general understanding of the error in GAT, as the corneal stiffness increases with CCT. A tear meniscus correction of 5 mmHg has been applied to all cases shown below. This accounts for IOPG values being lower than the corresponding IOPT values for the thinner corneas.

TABLE 6

IOPG Values (mmHg) by GAT (FE Simulation):

| CCT (nm) | IOPT = 11 mmHg | IOPT = 16 mmHg | IOPT = 24 mmHg |
|---|---|---|---|
| 450 | 9.9 | 14.6 | 21.9 |
| 550 | 11.5 | 16.0 | 23.3 |
| 900 | 18.4 | 22.2 | 28.7 |

Next, the proposed GA/NN method is applied to these nine cases to predict the IOPT values. A total of five GA runs were performed for each case. These five results again differ because each GA run starts with a completely random initial population. The mean and standard deviation (S.D.) of the predicted IOPT values from the five GA runs for each case are shown in Table 7.

TABLE 7

Mean (S.D.) of Predicted IOPT (mmHg) from Best Fitness Individual of Five GA/NN Runs:

| CCT (μm) | IOPT = 11 mmHg | IOPT = 16 mmHg | IOPT = 24 mmHg |
|---|---|---|---|
| 450 | 11.6 (1.74) | 15.3 (2.25) | 22.9 (1.82) |
| 550 | 10.5 (1.33) | 16.6 (1.25) | 22.2 (2.82) |
| 900 | 13.8 (2.66) | 16.1 (2.05) | 22.1 (1.82) |

The results shown in Table 7 show that the proposed GA/NN method reduces the error in GAT readings to an acceptable level.

Further insight can be gained by considering the application of the proposed method to a well known clinical case. Johnson et al., supra, report the case of a 17-year-old woman with an unusually high CCT (900 µm). Her clinical GAT readings were consistently very high (30-40 mmHg), which indicated that she was at high risk of developing glaucoma, even though she presented normal visual fields. After prolonged and unsuccessful treatment with medication to lower her intraocular pressure, her actual IOP was revealed by cannulation to be only 11 mmHg.

Figure 12:
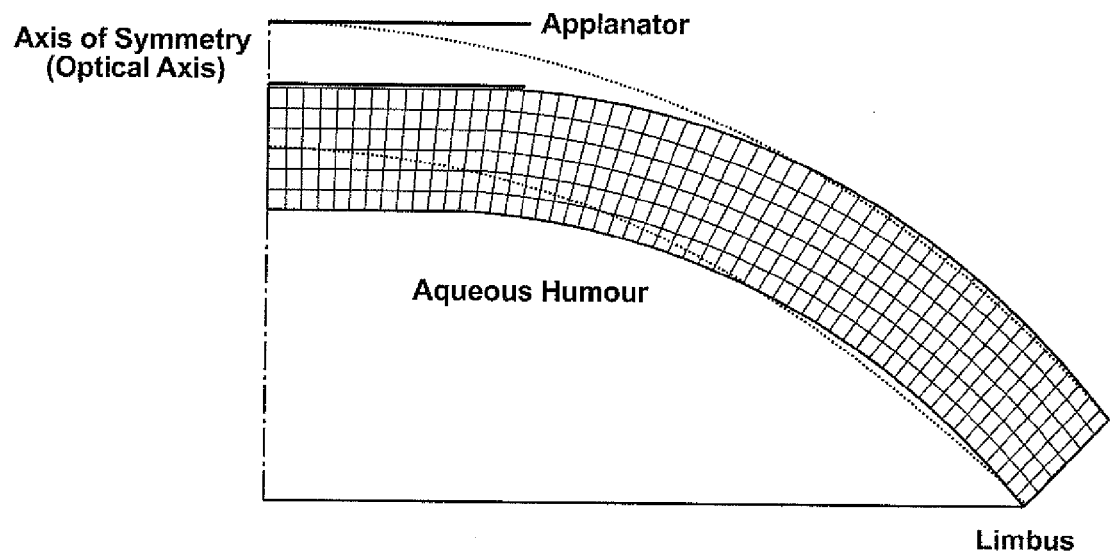
FIG. 12 is a graph showing a cross-sectional view of the deformed shape of an applanated cornea from GAT simulation of a clinical case in which CCT is 900 µm and the Goldmann applanation tonometer (IOPG) reading is 18.3 mmHg.

A FE cornea model with a CCT of 900 µm was developed according to Equation (1). Initially, Ep was assumed to be 0.23 MPa, with the other material parameters determined from the correlations mentioned previously. FIG. 12 is a graph showing a cross-sectional view of the deformed shape of the applanated cornea from GAT simulation of the clinical case just described. The Goldmann applanation tonometer (IOPG) reading is 18.3 mmHg.

Figure 13:
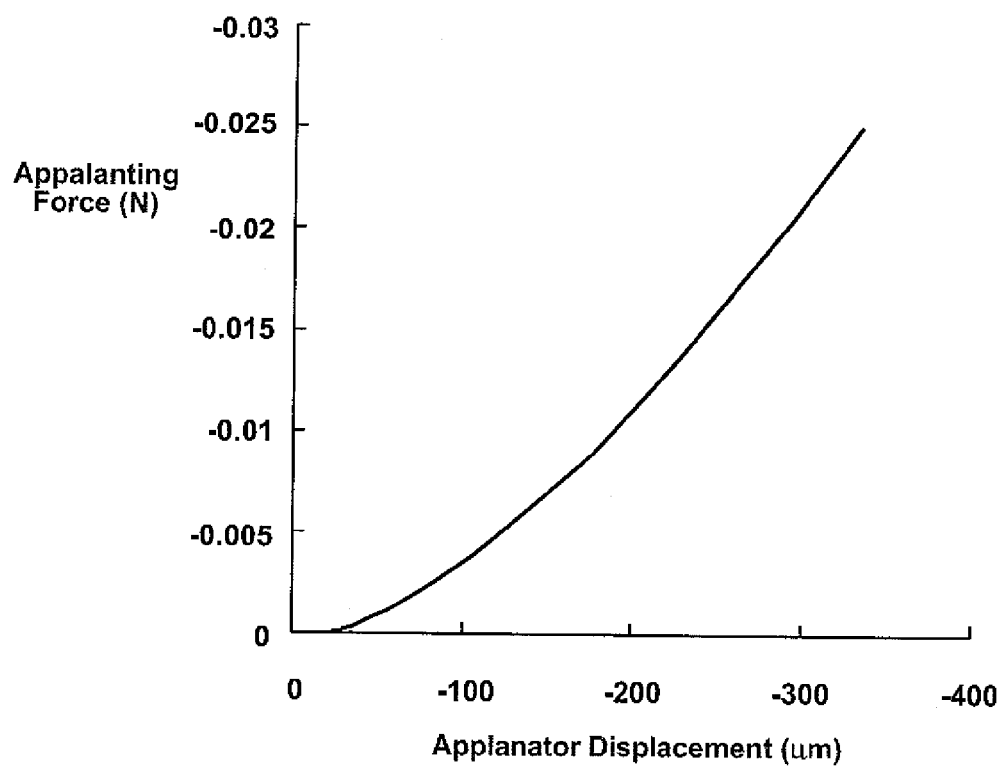
FIG. 13 is a graph showing a target response curve from synthetic GAT simulation of the clinical case of FIG. 12.

FIG. 13 is a graph showing a target response curve from synthetic GAT simulation of the clinical case of FIG. 12. This shows the applanator response history from the simulation. The simulated IOPG reading is 18.3 mmHg.

Figure 14:
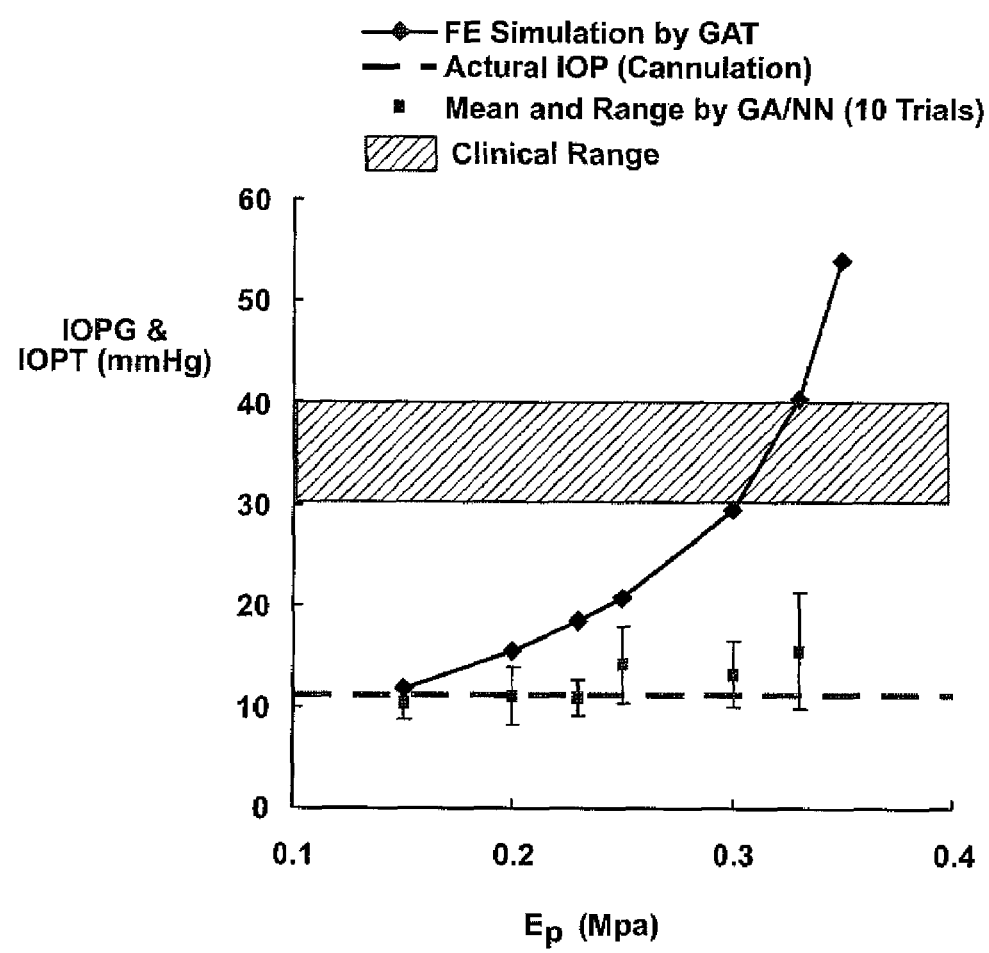
FIG. 14 is a graph showing an IOPT prediction by different methods for a clinical case with a CCT of 900 μm.

The actual cornea material properties, however, are not known in this clinical case; therefore six $E_p$ values, ranging from 0.15 MPa to 0.35 MPa were assumed. For each assumed value of $E_p$, the IOP by GAT (via FE simulation) was compared with that obtained by the proposed GA/NN method. FIG. 14 shows a comparison of these results.

FIG. 14 is a graph showing an IOPT prediction by different methods for a clinical case with a CCT of 900 µm. IOP predictions by the proposed method are satisfactory, in spite of the wide variation in the assumed material properties (represented by Ep) of the cornea. In FIG. 14, the filled square symbols representing IOP predictions by GA/NN are mean values from 10 runs and the bars indicate the mean plus or minus standard deviation (S.D.) of the GA/NN results. It might be inferred from FIG. 14 that the most appropriate value of $E_p$ for this particular clinical case is in the range 0.30~0.35 MPa since in that range the FE GAT simulation provides IOP estimates consistent with the clinical GAT readings of 30~40 mmHg as reported by Johnson et al., supra.

The effect of applying higher levels of applanating force is now discussed. The standard applanation response is obtained by applying force via the GAT until the diameter of the applanated area is equal to 3.06 mm. It is reasonable to expect that the response curve would contain more information if the applanating force was increased beyond the Goldmann force level. Of course, the applanating force must be kept within safe limits, and any proposal to increase its magnitude would have to be studied very carefully.

Figure 15:
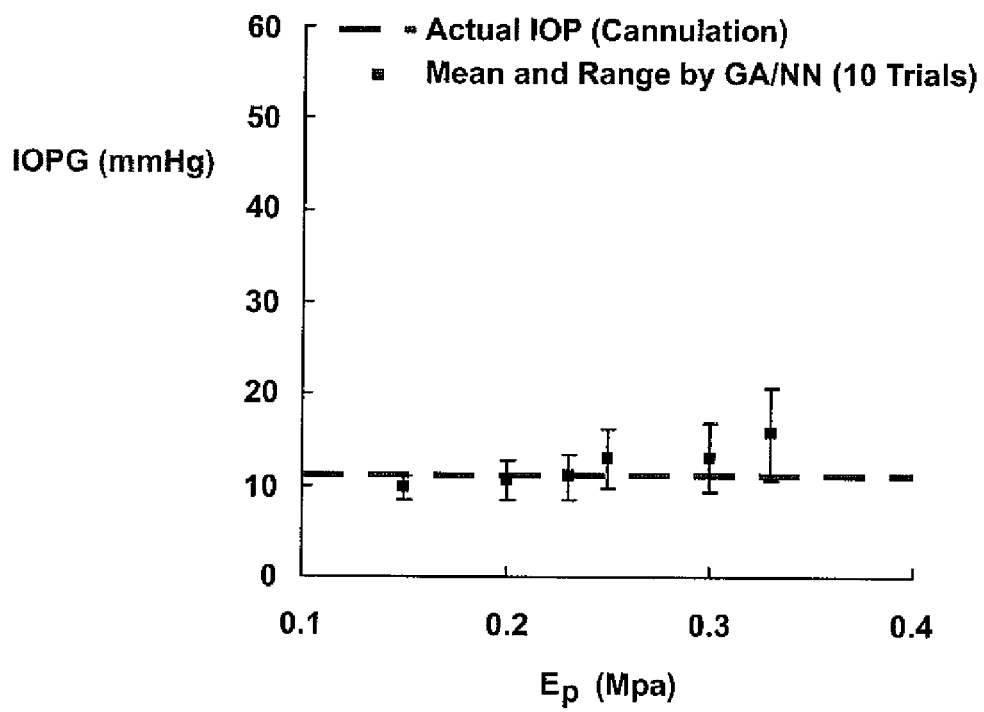
FIG. 15 is a graph showing an IOPT prediction by GA when the maximum applanating force corresponds to standard GAT from 10 trials at each $E_p$.
Figure 16:
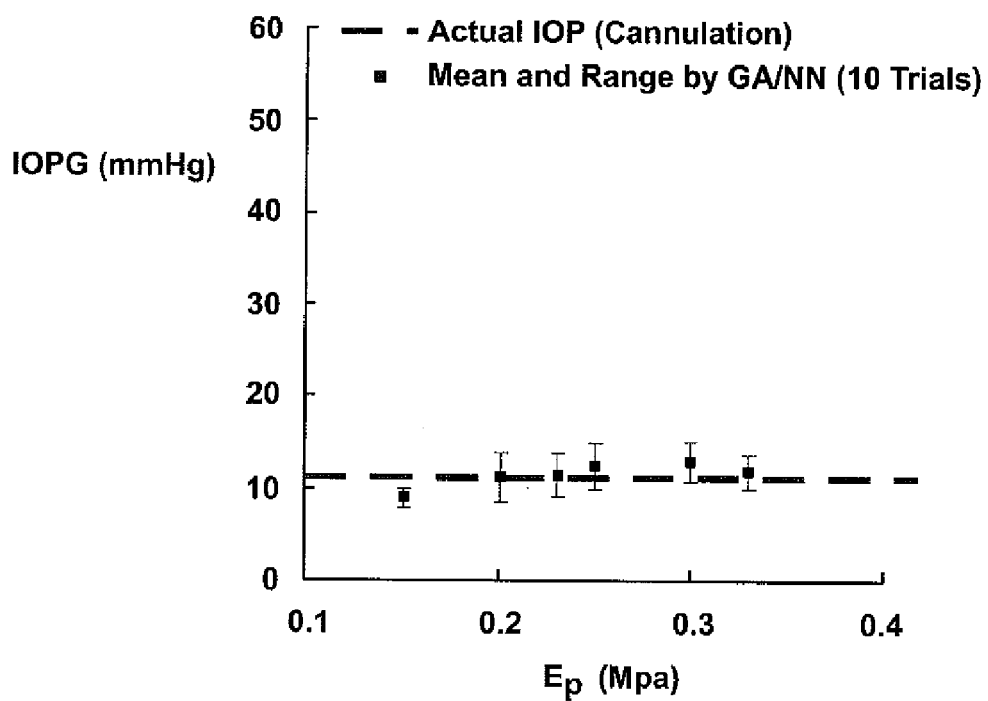
FIG. 16 is a graph showing IOPT prediction by GA when the maximum applanating force is 50% higher than standard GAT from 10 trials at each $E_p$.

FIGS. 15 and 16 show the results of a limited investigation of this hypothesis for the clinical case described above. FIG. 15 shows IOPT predictions by GA/NN obtained from the original standard applanation response (the same as FIG. 14). FIG. 16 shows IOPT predictions obtained from the applanation response curve computed by applying an applanating force 50 percent higher than the maximum GAT force level. The IOP predictions appear to be more accurate when the maximum applanating force is increased by 50 percent.

Material Characterization of Cornea by Self-learning Simulation (SelfSim).

Previously, practical tools to determine TOP with acceptable accuracy were introduced. The GA also has the demonstrated capacity to identify the material parameters for a postulated analytical (Extended Fung) material model. Although this nonlinear material model displays appropriate general characteristics, its applicability to modeling of the behavior of the human cornea remains to be more thoroughly verified.

Another approach to establishing a suitable individualized material model, which does not impose any preconceptions of how the cornea behaves, is to instead use neural network (NN) technology along with a self-learning algorithm, called the "Autoprogressive" algorithm, to learn this behavior directly from observed applanation response. For more in-depth discussion of the Autoprogressive algorithm, see U.S. application Ser. No. 10/409,882, filed Apr. 9, 2003 and entitled "Methods and Systems for Modeling Material Behavior" as applied to the design and construction of structures such as tunnels, underground sewers, foundations, buildings, etc. U.S. application Ser. No. 10/409,882 is assigned to the same assignee as the current application, and is hereby incorporated by reference. The Autoprogressive algorithm was later embodied in the SelfSim (Self-Learning Simulation) software platform.

The overall strategy is to first employ the GA/NN methodology described above to establish an accurate estimate of the true intraocular pressure (IOP), and then to use this estimated IOP as a known preload in SelfSim to extract the NN material model of the cornea. The two-step procedure may be used iteratively, but this possibility has not been investigated herein.

The measured input and output of any system can be used to develop a NN model of the behavior of its components. The SelfSim platform was developed for training a NN constitutive model from observations of the global response of a "structure," in this case the response of the cornea to applanation. In conventional parameter optimization techniques, parameters are selected so that the system response closely matches the measured response whereas in SelfSim, the NN material model is iteratively updated during successive load passes and gradually improves. Moreover, all of the parameter optimization techniques work within the framework of a pre-selected analytical material model formulation; in the Autoprogressive algorithm, the material stress-strain relationship is learned without the need for specifying an analytical framework.

A GAT simulation can be viewed as a structural test which provides the global structural response (applanating force versus apical displacement) history. SelfSim can be used to extract the NN representation of the cornea material model from this information.

A step in this procedure is to select an appropriate NN material model architecture to properly represent the cornea material behavior (i.e., selection of input and output node information). Because the cornea behavior strongly depends on the physiological stress (due to IOP), the NN model should have input nodes that specify the state of the physiological stress in addition to input nodes that specify the current strains.

The SelfSim algorithm is briefly described here for completeness. It has two distinct components: a self-learning neural network (NN) representation of material behavior and an algorithm for employing global response data to iteratively update the NN connection weights, thereby gradually improving the global response prediction accuracy.

Artificial neural networks (NNs) are very useful because of their functional mapping properties and their ability to learn from examples. The concept of using neural networks in constitutive modeling was introduced by Ghaboussi et al. (1991). The NN material model defines the relationship between stresses and strains (or their rates) as in conventional analytical material models. But it learns the constitutive material behavior directly from experimental data and stores that knowledge in its connection weights. This learning capability of NNs provides a fundamental new capability in modeling material behavior, i.e. the NN material model is able to generalize the specified experimental data but also continuously adapt to new data. Typically, current strains (or strain rates) are inputs to the neural network; additional inputs can be stress and strain histories in the case of history dependent materials. The output is typically current stresses or stress rates.

A general notation to compactly represent the NN architecture may be represented by:

$$\{\text{output parameters}\} \text{ NN } (\{\text{input parameters}\}; \{\text{NN architecture}\}). \quad (6)$$

The symbol NN stands for multi-layer feed forward neural network (NN) which is the most common choice for NN material modeling. The first argument in equation 6 specifies the input variables to the NN. It includes current strains and additional inputs for previous stress and strain in case of history dependent materials. The second argument describes the NN architecture represented by a number of nodes at each layer. "Output parameters" usually indicate stresses as the outputs of the NN.

Figure 17:
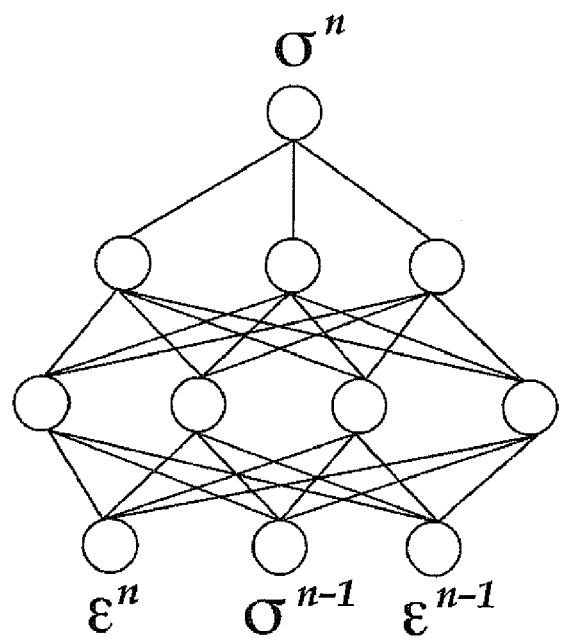
FIG. 17 is a typical network material model which is history dependent.

FIG. 17 shows the architecture of a typical neural network material model which is one-dimensional and history dependent. Equation 7 shows the symbolic notation representing the neural network model in FIG. 17.

$$\sigma^n = \sigma \, NN \, (\epsilon^n, \sigma^{n-1}, \epsilon^{n-1}; 3\text{-}4\text{-}3\text{-}1) \quad (7)$$

Neural network (NN) material models can use their learning capability to model constitutive behavior using information from material (i.e., specimen) tests, which are usually intentionally designed to result in states of stress or strain in the specimen that are spatially uniform, or nearly so. This approach may require a large amount of experimental data for different applied loading patterns or combinations thereof in order to successfully develop a comprehensive material model.

In contrast to such conventional specimen tests, global tests on complete structures generally produce stress and strain fields in the structure and its components that are not spatially uniform; global response data from such tests is therefore much richer in information than response data from material (specimen) tests.

The Autoprogressive algorithm provides an effective means for extracting and utilizing this information from global tests to essentially provide, from even a single global test, a wide spectrum of cases for NN training. This algorithm which was developed by Ghaboussi et al. (1998) provides the fundamental basis for development of the SelfSim software platform. The algorithm uses the partially-trained neural network (NN) in an iterative non-linear finite element (FE) analysis of the test structure in order to extract approximate, but gradually improving, stress-strain information with which to further train the neural network.

In order to get the algorithm started, the NN material model must be pre-trained. While there is some freedom in selecting pre-training cases with which to initialize the NN, it has been found convenient to use cases generated from a linear elastic constitutive model. This initial behavioral description does not have to be exact because the pre-training data is excluded from updated training data after a few loading stages of the Autoprogressive non-linear FE simulation, and is therefore eventually "forgotten" by the neural network.

Figure 18A:
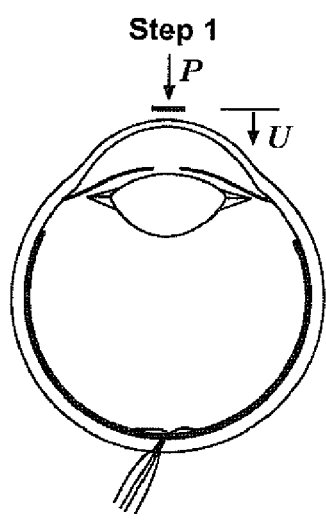
FIGS. 18A, 18B, and 18C display a series of steps defining an Autoprogressive algorithm training framework.
Figure 18A:
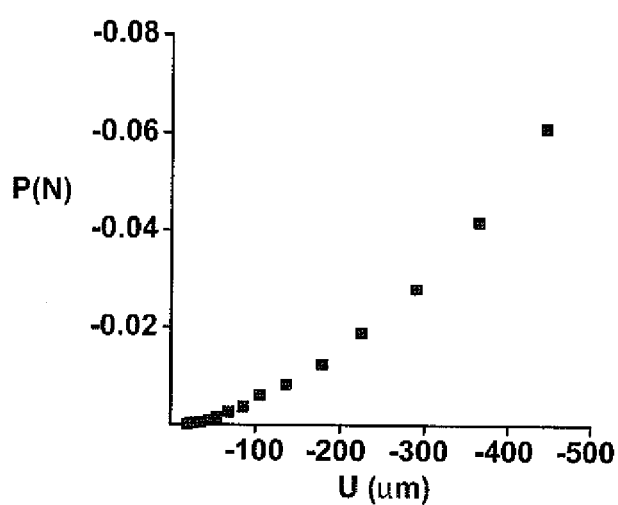
Figure 18B:
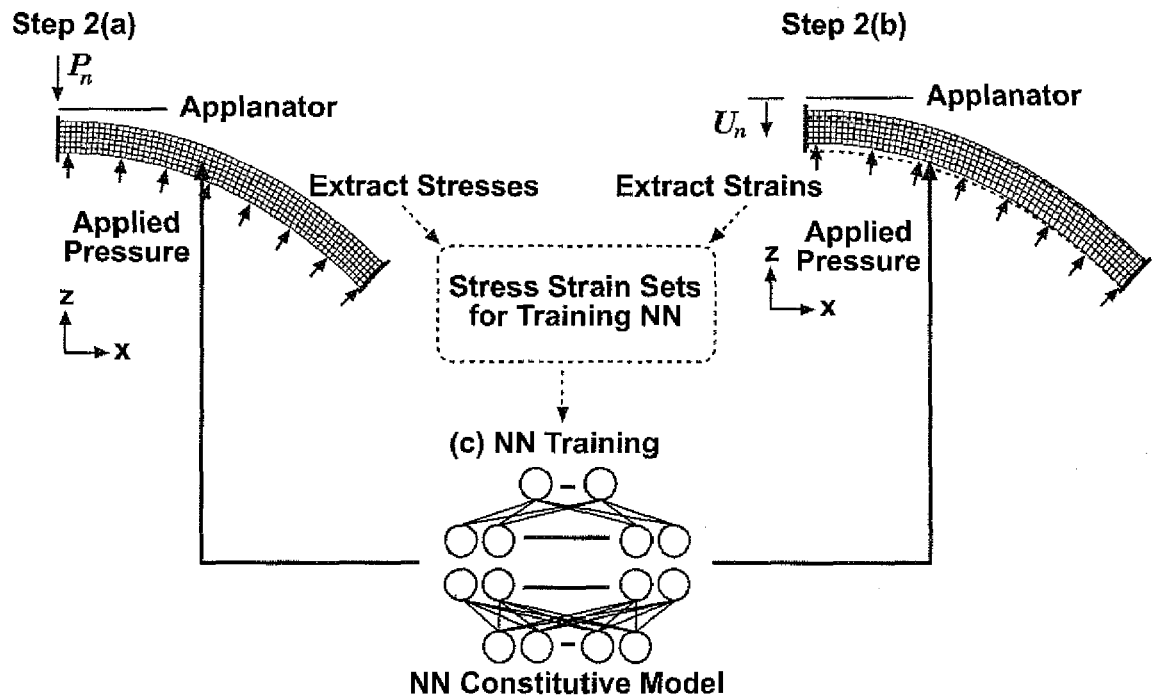
Figure 18C:
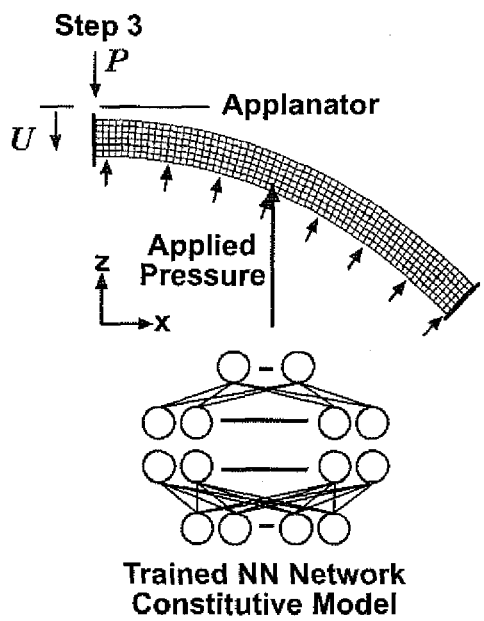

FIGS. 18A, 18B, and 18C display a series of steps defining an Autoprogressive algorithm training framework. A structural test provides two complementary boundary measurements of loads and displacements as illustrated in FIG. 18A, step 1. This structural test is of the actual cornea taken in a laboratory or in the field. In FIG. 18B, or step 2, the structural test is computer simulated by applying the global load (or displacement) incrementally. For each load increment, two FE structural analyses are performed using the partially trained neural network material model. The label P indicates pressure and the label U indicates displacement.

In step 2(a) of FIG. 18B the measured loads are applied to a FE analysis with a NN material model. The resulting stress field provides an acceptable approximation of the actual stress field because the measured loads are used and equilibrium is satisfied. The resulting strain field in step 2(a) is considered to be a poor approximation of the actual strain field because the resulting displacements do not match measured displacements. In step 2(b) of FIG. 18B the measured displacements are imposed to a FE analysis with the same NN material model. The resulting strain field provides an acceptable approximation of the actual strain field because the measured displacements are used and compatibility is satisfied. The resulting stress field in step 2(b) is considered to be a poor approximation of the actual stress field because the resulting loads do not match measured loads.

Figure 18D:
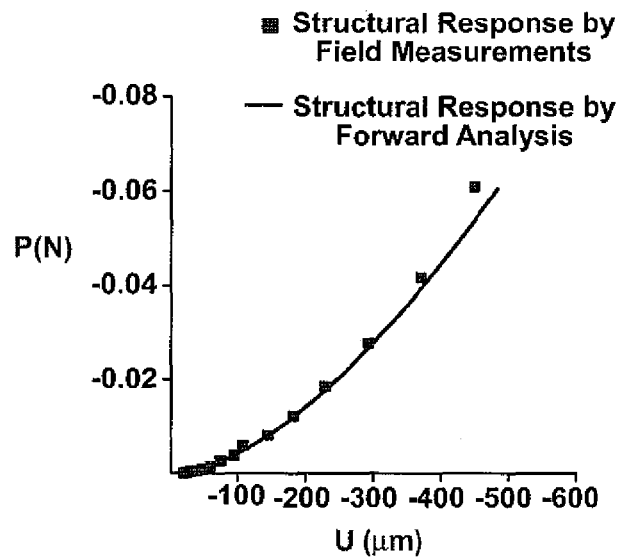
FIG. 18D displays a graph comparing the structural response by field measurements with the structural response by forward analysis that uses the Autoprogressive algorithm and computer simulations as shown in FIGS. 18B and 18C.

FIG. 18D displays a graph comparing the structural response by field measurements with the structural response by forward analysis that uses the Autoprogressive algorithm and computer simulations. Note that the two follow closely and slightly diverge at large displacements and pressures.

Stress-strain sets from steps 2(a) and 2(b) are collected to update the NN connection weights at a given loading stage. This entire process (two FE analyses and updating neural network weights), is called a "cycle." Several cycles can be repeated to satisfy the error criteria within the given loading stage. The entire sequence of loading stages for the structural test is termed a "pass." Usually, a NN material model will continue to improve with additional passes, until the material behavior has been learned sufficiently well that the global structural response is closely matched by a "forward" analysis (one in which the connection weights of the NN material model are frozen, and no additional training takes place).

The SelfSim software platform employs the Autoprogressive algorithm and incorporates many additional features such as a graphical user interface and utilities for handling the large collection of continuously evolving stress and strain sets training sets. For example, the NN can be reinitialized at any time during the training if it helps to develop better stress and strain sets.

Figure 19:
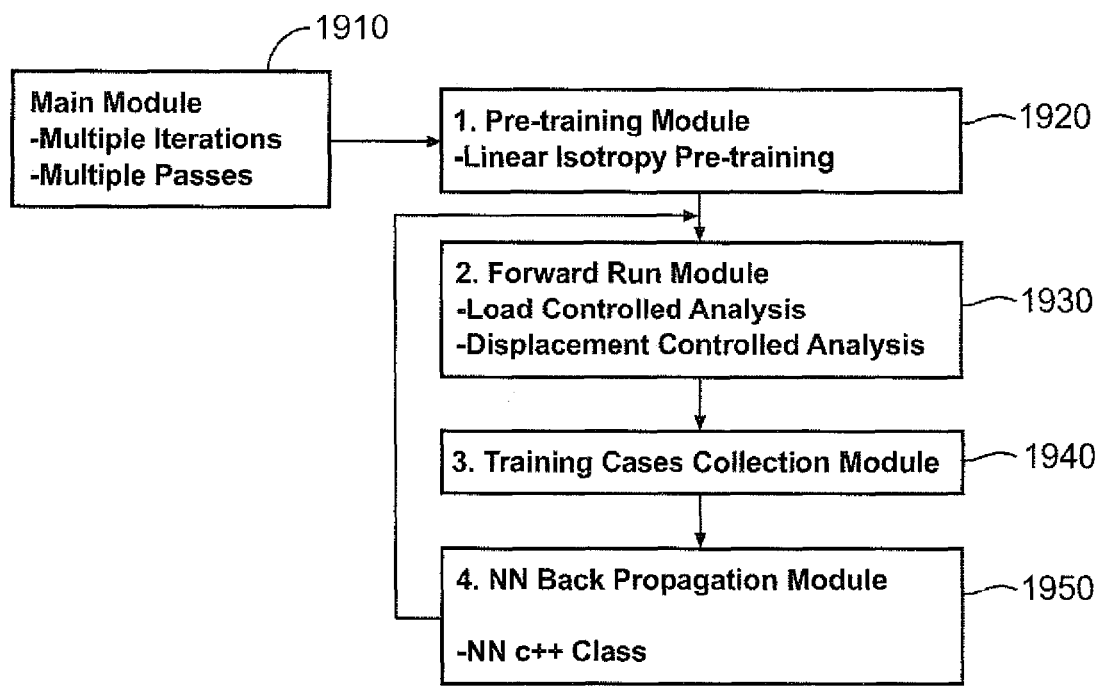
FIG. 19 is a flowchart for material characterization of the cornea by self-learning simulation (SelfSim).

FIG. 19 is a flowchart for material characterization of the cornea by self-learning simulation (SelfSim), which may be programmed in C++ and include separate modules, as shown. The commercial package ABAQUS 6.3.1 may be used for the FE analysis in the Forward Run Module. At block 1910, a main module is provided to track multiple iterations or cycles and multiples passes of the Autoprogressive algorithm as discussed. At block 1920, a Pre-training Module conducts whatever pre-training is necessary. The type of pre-training found to be most productive is to pre-train on a data set from a linear elastic constitutive model, linearly isotropic. The pre-training data is later excluded from the evolving training set generated via the Autoprogressive algorithm in SelfSim (discussed below). At block 1930, a Forward Run Module includes load controlled analysis and displacement controlled analysis to conduct forward analysis using the Autoprogressive algorithm. At block 1940, a third module is for collecting data from the training cases. At block 1950, a NN Back Propagation Module provides updated sets of strain and stress data back into the Forward Run Module in order to iteratively produce increasingly more accurate material parameters of the cornea.

The determination of a NN material model from synthetic GAT applanation response data using SelfSim is now described. It is assumed that the true TOP is known. Synthetic target data is used for initial development and evaluation for several practical reasons which have already been discussed.

Figure 20A:
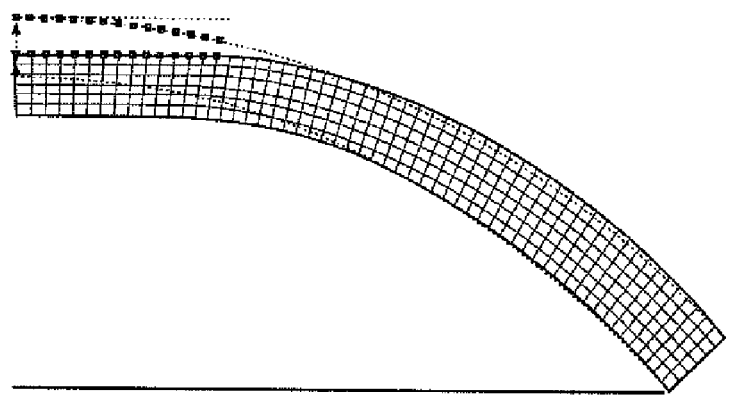
FIGS. 20A and 20B are respectively a synthetic target applanated cornea and target response of the applanated cornea.
Figure 20B:
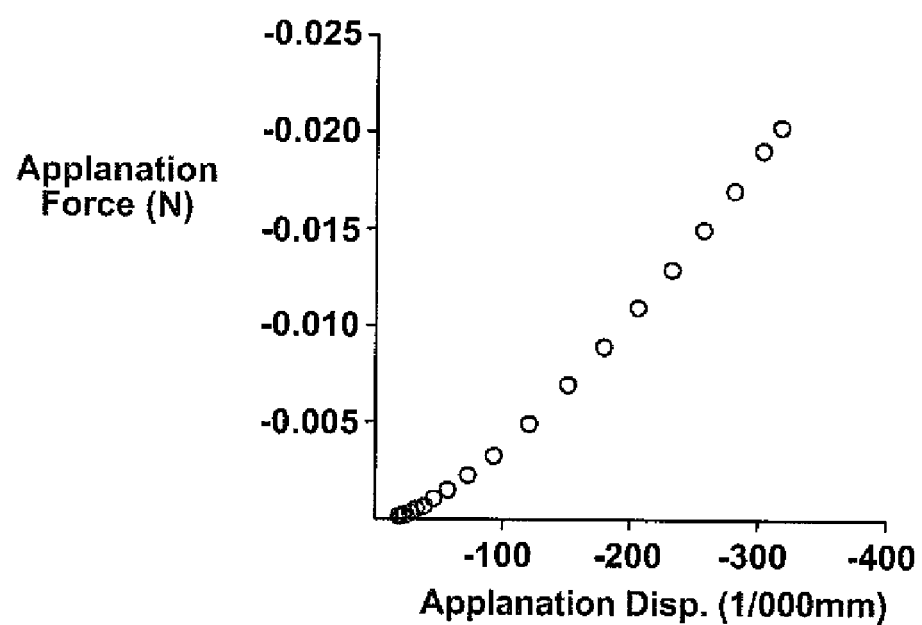

FIGS. 20A and 20B respectively show a synthetic target applanated cornea and a target response of the applanated cornea. The synthetic target response is determined by FE GAT simulation for CCT=500 μm, IOP=15 mmHg, using the analytical Extended Fung material model with $E_p$=0.23 MPa. FIG. 20A shows the applanated shape for the target case while FIG. 20B shows the target applanation response (applanation force versus displacement of the cornea).

A new simulation-based methodology for accurate determination of intraocular pressure is proposed. The methodology uses a combination of genetic algorithm (GA) and neural networks (NN) to minimize the difference between the measured applanation response history and the response history obtained from a finite element (FE) simulation of Goldmann applanation tonometry. The performance of the proposed method has been demonstrated through a parametric study and by comparisons with a well-known clinical case reported in the literature. See Johnson et al., supra. The results show significant improvement compared to uncorrected Goldmann applanation tonometry. The proposed method is computationally efficient because a trained NN is used within the GA to replace the large number of nonlinear FE simulations needed for fitness evaluation.

Characterization of mechanical properties of the individual human cornea will make it possible to fine tune laser refractive surgery and improve its outcome. This can be done through virtual surgery. A significant number of laser refractive surgeries, including LASIK, intended to improve a patient's vision lead to sub-optimal results that affect peripheral and night vision. A smaller number of laser refractive surgeries lead to medical complications. This disclosure will allow development of individualized laser refractive surgeries based on the measured mechanical properties of each individual cornea, thus avoiding sub-optimal results and certain medical complications.

Although the focus of the present disclosure has been on determination of intraocular pressure (IOP), the proposed GA/NN methodology may also be used to (1) calibrate specific corneal material models, and (2) estimate central corneal thickness. The broader applications of the methodology are in minimally invasive in vivo quantitative characterization of the mechanical properties of soft tissues in general. Quantitative characterization of the mechanical properties of soft tissue not only will have important applications in biomedical research, it will also have clinical applications in disease diagnosis, monitoring, and virtual surgery. Monitoring the mechanical properties of the human cornea also has potential application in diagnosis and disease progression. These latter potential applications are part of the broader impact of the proposed methods.

The terms and descriptions used herein are set forth by way of illustration only and are not meant as limitations. Those skilled in the art will recognize that many variations can be made to the details of the above-described embodiments without departing from the underlying principles of the disclosure. The scope of the disclosure should therefore be determined only by the following claims (and their equivalents) in which all terms are to be understood in their broadest reasonable sense unless otherwise indicated.

The methods disclosed herein include one or more steps or actions for performing the described methods. The method steps and/or actions may be interchanged with one another. In other words, unless a specific order of steps or actions is required for proper operation of the embodiment, the order, and/or use of specific steps, and/or actions may be modified without departing from the scope of the disclosure.

The embodiments may include various steps, which may be embodied in machine-executable instructions to be executed by a general-purpose or special-purpose computer (or other electronic device). Alternatively, the steps may be performed by hardware components that contain specific logic for performing the steps, or by any combination of hardware, software, and/or firmware.

Embodiments may also be provided as a computer program product including a machine-readable medium having stored thereon instructions that may be used to program a computer (or other electronic device) to perform processes or methods described herein. The machine-readable medium may include, but is not limited to, floppy diskettes, optical disks, CD-ROMs, DVD-ROMs, ROMs, RAMs, EPROMs, EEPROMs, magnetic or optical cards, propagation media or other type of media/machine-readable medium suitable for storing electronic instructions. For example, instructions for performing described processes may be transferred from a remote computer (e.g., a server) to a requesting computer (e.g., a client) by way of data signals embodied in a carrier wave or other propagation medium via a communication link (e.g., network connection).

The invention claimed is:

1. A computer-implemented method for accurate determination of intraocular pressure (IOP) and characterization of mechanical properties of a cornea, comprising:
   measuring the cornea with a probe tonometer to produce at least force versus displacement data over a range of applied forces, the probe tonometer applying a small force directly to a surface of the cornea; and
   forming a model of corneal constitutive parameters of the cornea with a computer including a processor and coupled with the probe tonometer, the model based on the data obtained by the probe tonometer to more accurately determine IOP and to characterize mechanical properties of the cornea including non-linear anisotropic properties;
   wherein forming the model comprises:
      determining a plurality of in situ stresses and corresponding strains in the cornea subject to IOP; and
      modeling a target response of applanation tonometry by simulation of the computer by combining, at each of a plurality of material force reference points, the modeled corneal constitutive parameters and the plurality of strains.

2. The method of claim 1, wherein determining the plurality of in situ stresses in the cornea subject to IOP comprises: artificially increasing the initial linear stiffness of the cornea by a suitable factor; and applying intraocular pressure (IOP) in computational simulation to determine in situ stresses which equilibrate the IOP;
   the method further comprising determining, at each of the plurality of material force reference points, the plurality of strains that would be consistent with the set of in situ stresses by use of an iterative numerical process.

3. The method of claim 1, further comprising:
   executing a genetic algorithm (GA) by the computer to determine an individual IOP finite element (FE) response that substantially produces the target response of the cornea under applanation; and determining from the individual IOP FE response a set of IOP and cornea nonlinear elastic material parameters.

4. The method of claim 3, wherein the GA comprises a string of encoded variables that represent variables in a function that defines a curve of the target response to be produced.

5. The method of claim 4, wherein the variables that are encoded comprise IOP, the modeled corneal constitutive parameters, and central corneal thickness (CCT).

6. The method of claim 3, further comprising:
maximizing a fitness function that comprises an inverse of the difference between the applanator displacements from the FE response and target applanator displacements generated by masked FE simulation.

7. The method of claim 6, wherein the fitness function comprises:

$$F = \frac{1}{1 + \sum_{i=1}^{N} \frac{|\text{Individual Response}_i - \text{Target Response}_i|}{|\text{Target Response}_i|}},$$

where N is a number of discrete points on a curve of the applanator response.

8. The method of claim 3, wherein the individual IOP FE response comprises a simulated FE probe tonometer or Goldmann Applanation Tonometer (GAT) response calculated through a trained neural network.

9. The method of claim 1, further comprising:
iteratively performing:
randomly selecting from a set of variables, within a predetermined range, that include a plurality of modeled corneal material parameters, central corneal thickness (CCT), and IOPT;
checking stability of the plurality of modeled corneal material parameters for the corneal model to ensure that an initial tangent stiffness matrix is positive definite;
running a GAT or probe tonometer simulation using the predetermined set of variables; and
collecting sets of outputs of applanator displacement $d_i$ corresponding to applanating force $p_i$;
calculating a mean-squared-error function ($E_{MSE}$) from a comparison between the target response and the sets of outputs $d_i$, $p_i$; and
adjusting the randomly selected set of variables to train a neural network (NN) to converge on a curve of the target response.

10. The method of claim 9, further comprising:
executing a genetic algorithm (GA) that uses as its input the sets of outputs $d_i$, $p_i$, to determine an individual IOP response that substantially produces the target response of the cornea under applanation.

11. The method of claim 10, further comprising:
determining from the individual IOP response a set of IOP and cornea nonlinear elastic material parameters.

* * * * *